US006540664B1

(12) United States Patent
Blair

(10) Patent No.: US 6,540,664 B1
(45) Date of Patent: Apr. 1, 2003

(54) APPARATUS FOR FACILITATING ANALYSIS OF DREAM ACTIVITY

(76) Inventor: Bruce Blair, Apt. 408, 732 W. Bittersweet Pl., Chicago, IL (US) 60601

( * ) Notice: Subject to any disclaimer, the term of this patent is extended or adjusted under 35 U.S.C. 154(b) by 122 days.

(21) Appl. No.: 09/722,173

(22) Filed: Nov. 24, 2000

Related U.S. Application Data

(60) Provisional application No. 60/167,564, filed on Nov. 26, 1999.

(51) Int. Cl.$^7$ .......................... A61M 21/00; A61B 19/00
(52) U.S. Cl. ........................... 600/27; 600/28; 128/898
(58) Field of Search ..................... 600/27, 28; 368/246; 968/815, 967, 239, 231, 244, 588; 128/897

(56) References Cited

U.S. PATENT DOCUMENTS

| | | | | |
|---|---|---|---|---|
| 4,047,377 A | * | 9/1977 | Banks, Jr. ................. | 58/152 B |
| 4,228,806 A | * | 10/1980 | Lidow ......................... | 368/12 |
| 4,735,199 A | * | 4/1988 | DiLullo ....................... | 600/28 |
| 4,832,050 A | * | 5/1989 | DiLullo ................... | 340/573.1 |
| 4,863,259 A | * | 9/1989 | Schneider et al. .......... | 351/209 |
| 5,197,941 A | * | 3/1993 | Whitaker ..................... | 600/27 |
| 5,507,716 A | * | 4/1996 | LaBerge et al. .............. | 600/27 |
| 5,551,879 A | * | 9/1996 | Raynie et al. .............. | 434/236 |
| 6,058,939 A | * | 5/2000 | Goldsmith ................. | 128/898 |
| 6,272,378 B1 | * | 8/2001 | Baumgart-Schmitt ....... | 600/544 |

FOREIGN PATENT DOCUMENTS

WO          WO 91/16853         * 11/1991

* cited by examiner

Primary Examiner—William C. Doerrler
(74) Attorney, Agent, or Firm—Michael Best & Best LLC

(57) ABSTRACT

An assembly (18) comprises an insert casing (30) and an outer casing (28). The inner casing comprises the device output LED diodes (54a), (56a) and (58a), the LCD display screen (42), the Speakers (50a), and device input Microphones (46a and 52a), Device Reset button (48a), Sound Playback button (50a) and program input Key press buttons (34a), (36A.) and (40a). A Voice activation switch (64) operating a voice recording chip (66) is activated during REM alerts (20) by a micro controller (62) and a backlight (not shown) for and LCD display screen (42).

20 Claims, 14 Drawing Sheets

APPARATUS FOR FACILITATING ANALYSIS OF DREAM ACTIVITY

RELATED APPLICATIONS

This application claims priority of Provisional Patent Application Ser. No. 60/167,564 filed on Nov. 26, 1999.

BACKGROUND OF THE INVENTION

The present invention provides a method and apparatus enabling a user to investigate his or her nightly dream activity with little or no loss in the restorative process of a good night's sleep.

The use of dreams as an anecdotal source of inspiration and prophecy is so common as to be recognizable across cultures, both current and through the ages. Mythological references to dreams and their effects abound. More recently, dreams have been made the basis of mental health inquiries through psychoanalysis. Individuals discussing their dreams with family and friends is an experience shared by all. Many inventors, scientists and artists have reported dream activity as the basis of many of their creative accomplishments.

Many devices have been developed over the years to analyze dreams and enhance the dreamer's memory of his or her dreams. However, the prior art has mainly focused on one notable aspect of dream activity: the so-called "Lucid Dream". The lucid dream is a dream in which the dreamer is aware of dreaming while remaining in the dream state. This arcane condition is often the focus of sleep labs and research institutes. Such facilities have developed devices to sense a sleeper's dreaming or non-dreaming state.

In general these devices sense the test subject's dream state. When a dream state is detected some form of feedback is provided to alert the patient to fact that a dream is occurring. If all works out well, a lucid dream will ensue. Prior art devices all require some form of physical device that attaches to the patient. Wearing such an attachment is not a normal part of the patients sleep habits and can interfere with the test subject's usual night's sleeping process and may itself become the focus of the subject's dream activity.

For example, U.S. Pat. No. 5,507,716 to LaBerge et al. discloses a mask, similar to sunglasses or goggles, which is additionally wired for sound. Such an item may be suitable for investigating sleep patterns in a lab context, but it is not likely to find widespread nightly usage among the general populous. Additionally, the Laberge et al. devices are expensive, further limiting their appeal to individuals who may desire to investigate their dreams on their own.

Many experiments have been performed to awaken test subjects during the so-called REM (Rapid Eye Movement) periods of sleep. It has been determined that these periods usually correspond with dream activity. When a test subject is awakened during a REM event, the subject is usually able to remember the dream which was occurring at the time he or she was awakened. If the test subject is not awakened, the dream is more likely to be forgotten during intervening periods of deeper, dreamless sleep. Thus, for those individuals who are interested in investigating the subjects of their dreams it is desirable that they occasionally be woken up either during or shortly after a REM event.

With most subjects, the first REM event usually occurs about sixty minutes after the subject falls asleep. Thereafter, periods of deep sleep with little dream activity are punctuated by periods of heightened dream activity during REM events which occur approximately every 90 minutes. Three to five dreams may be associated with each REM event. These cycles are usually consistent for a given individual but vary widely from one person to another. In a substantial percentage of the population the rhythms are so strong and consistent that many people have no need for an alarm clock. Their own "internal clocks" are so accurate that they wake up at the same time each morning on their own. This indicates that for many individuals it is not necessary to provide sensors and or physical hookups to the individual to determine when REM events are taking place since the REM events will take place at substantially the same time each night.

For those persons having a sufficiently regular sleeping rhythm, a remote device could be programmed to wake the individual at the appropriate times at the end of or just after the conclusion of REM events. Such a device could be configured to wake the dreaming individual by issuing a "dream alert" in the form of flashing lights, sounding an alarm, playing music, and so forth. Such a device would ideally allow for variable time settings in order to individually synchronize the occurrence of dream alerts with individual's nightly rhythms. Dream alerts could be set to occur, for example, at the end of the individual's REM events or shortly thereafter.

Such synchronization could be effected through repeated use and fine tuning of the dream alert settings. Reliable timing will proceed from the daily stored and updated values of the alert variables. By fine tuning the synchronization between the dream alerts and the occurrence of REM events, the dream alerts may be provided by a remote device with no physical connections to the user. The user would then experience a more natural sleep environment while still benefiting from being awakened during or shortly after REM events so that dreams are more fully remembered. An additional desirable feature of such a device would be to include a dictation system so that the user could record the subject matter of his or her dreams before returning to sleep. Further, the user's normal sleep patterns such as the time the individual normally goes to bed and gets up should be storable so that the user need not go through a tedious set up procedure each night before retiring. The nature of the dream alerts should also be selectable to allow for a wide range of wake up options. For example, device settings should allow for minimal intrusion during the REM cycle. This will help to prevent waking the user during NON-REM periods, as well allowing the user to complete dreams before the dream alert awakens the user.

SUMMARY OF THE INVENTION

The present invention relates to an apparatus for facilitating the investigation of the subject matter of dreams. The apparatus of present invention relies on the pregrogrammed time settings which are calculated to correspond to the occurrence of REM events that occur throughout the night while the user is sleeping. It is during such REM events that most dream activity occurs. Because the apparatus calculates when REM events are expected to occur rather than sensing REM events directly, the apparatus may be completely remote from the user. Thus, no attachments are required which may otherwise interfere with the user's sleep. The apparatus wakes the user during the calculated REM events by flashing LEDs, or other means. When the user is awakened, a voice activated dictation system may be employed so that the user may orally record the details of the dreams that where happening when the he or she was awakened.

The apparatus includes a pair of mircro controllers. A first micro controller receives input in the form of various pushbutton switches, and also drives the output which drive LEDs or other alarms used to wake the user. The second micro controller is used to drive an LCD screen with prompts the user to enter various data necessary to program the apparatus and set up the various alarms that will wake the user during the course of the night. The LCD also acts to display previously selected settings.

In an embodiment of the invention, dream alerts comprise a plurality of flashing LEDs. The LEDs may be a combinationi blue red and green LEDs so that the over all color of the flashing lights may be selectable. Furthermore, the intensity, the length of the pulses and length of time between the pulses may also be selectable and the intensity of the pulses may be subjected to a ramping function. The first micro controller is programmed to receive a start time corresponding to a time when the user goes to sleep and an end time corresponding to a time when the user expects to rise. From these times the micro controller calculatest the times at which the user is likely to be experiencing REM events, based on 4, 5 and 6 REM event cycles. The user may then select whether he or she wishes to receiv dream alerts at the various times calculated by the micro controller. The dream alerts are temporally related to the occurrence of the REM events in that they are scheduled to occur at a time during the actual occurrence of the REM events.

OBJECTS AND ADVANTAGES

Accordingly, besides the objects and advantages for the dream analyzer described above, several further objects and advantages are, as noted:

(a) to provide an alert interface with the following adjustable values: the number of total pulses, the intensity of the pulses, the length of pulse time on, the length of time between pulses, the color of the pulse, and a controllable oscillation of the pulse intensity.

(b) to provide the previously entered alert values as the default values for the night's alerts. The user thus gravitates to values which are consistent and reliable over time.

(c) to provide a programmable alert interface. Unlike all previous prior art, an interface allows the user to interactively select not one but three sets of alert notification. Three separate sets of alert values are provided to allow for three different sets of alerts for the beginning, middle and final night's dreams. This allows for the maximum use of the device if a user intends more than one alert per night activity.

(d) to provide oral notation recording. As the individual must not move during an awakening or a dream will be lost, a voice chip recorder will be activated for a short period to allow a dreamer to voice his or her dream description. This may be reviewed with manual operation on the morning's arising.

DETAILED DESCRIPTION OF INVENTION

Figure 1:
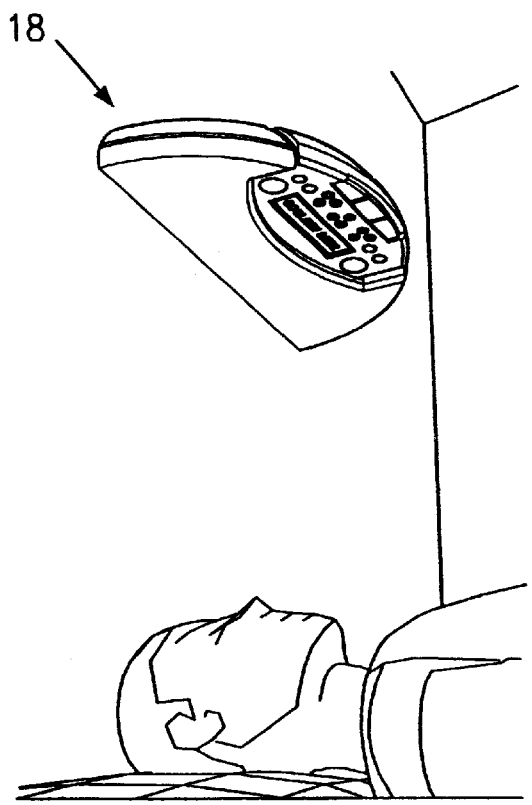
FIG. 1 is a perspective view of a dream analyzer according to an embodiment of the invention which is in use.

In FIG. 1, an apparatus 18 for analyzing dreams is mounted to a wall or the head board of a bead above the individual 16 using the apparatus. The apparatus for analyzing dreams 18 operates to wake the individual 16 sleeping below the device at predetermined times corresponding to the individual's nightly REM cycle. By waking the individual 16 during or at the end of a REM event the individual is more likely to remember the details of the dream or dreams that occurred during the REM event than if the individual remained sleeping. The dream analyzer includes a voice activated dictation system whereby, upon waking up during or shortly after a dream, the individual 16 may dictate a description of the dream to the apparatus 18. In this way, many vivid details of the dreams that are normally forgotten when the individual goes back to sleep may be preserved. The dream analyzer 18 records the individual's spoken message for later playback when the individual is awake.

The dream analyzer 18 is fully programmable so that the individual 16 using the device can customize its functions to adapt the machine to his or her individualized sleeping patterns. Optimal results are achieved when the individual using the apparatus follows a regular sleep pattern, going to bed at or near the same time each evening, and rising at substantially the same time each morning. Under these conditions, REM events are most likely to occur at or near the same times each night.

In order to fully appreciate the operation of the dream analyzer 18 of the present invention, it is first necessary to review various sleeping patterns common to most people. The age of a user will usually determine most of the timing settings. Infants spend nearly half of sleep in REM. Older children and younger adults may require up to 10 hours of sleep, while the elderly require, on average, 6 or even fewer hours of sleep a night. Thus, a 6 to 10 hour length of sleep delineates the range of the user sleep period for the Home Sleep Lab.

Figure 2A:
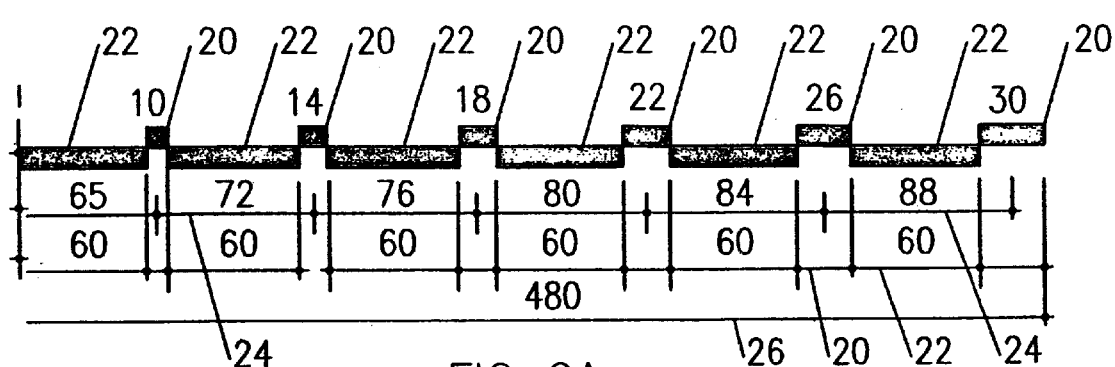
FIG. 2a and FIG. 2b illustrate the periodicity of dream intervals with six REM events within an eight hour and six hour period respectively.
Figure 2B:
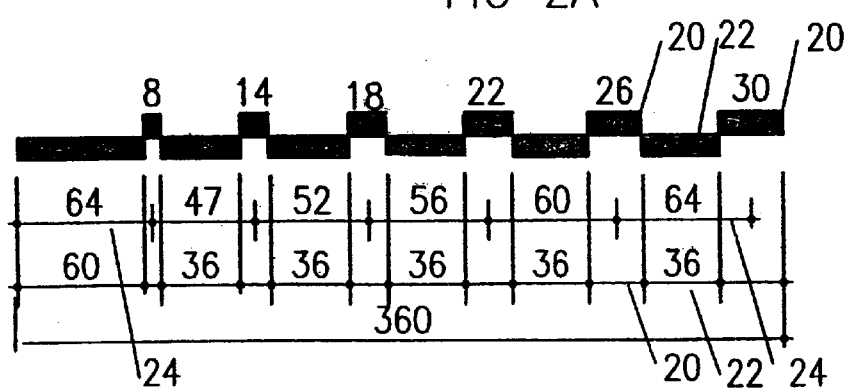
Figure 3A:
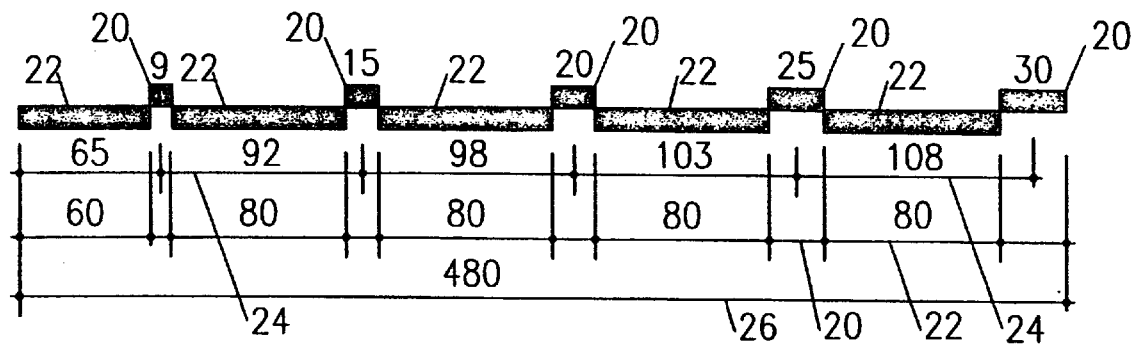
FIG. 3a and FIG. 3b illustrate the periodicity of dream intervals with five REM events within an eight hour and six hour period respectively.
Figure 3B:
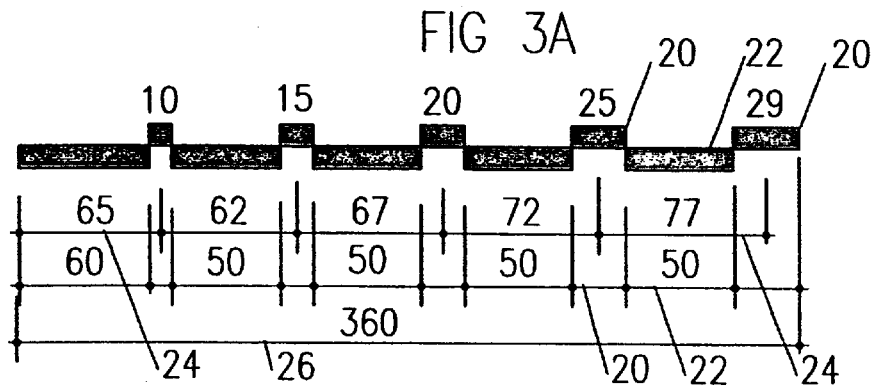
Figure 4A:
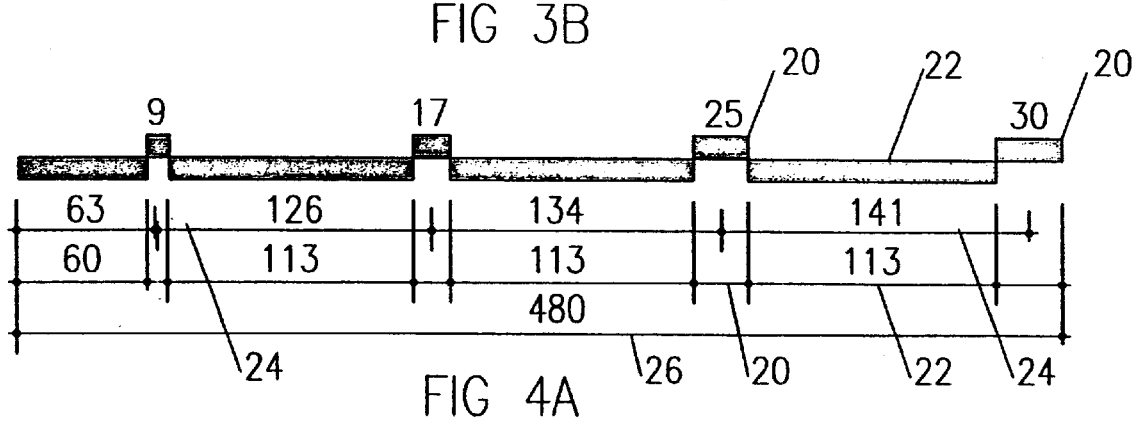
FIG. 4a and FIG. 4b illustrate the periodicity of dream intervals with four REM events within an eight hour and six hour period respectively.
Figure 4B:
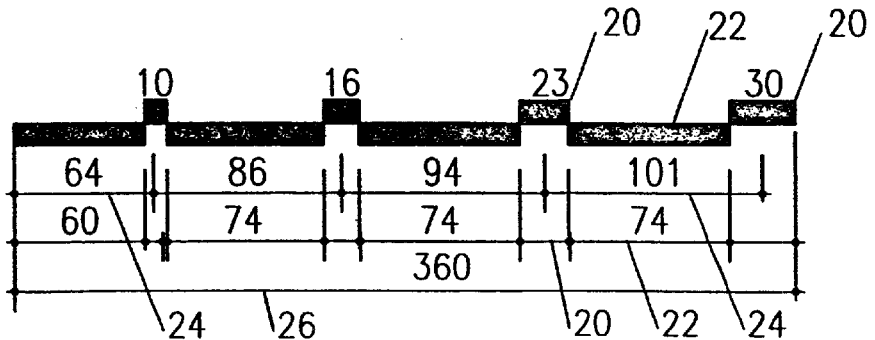

Most people follow a 4, 5 or 6 REM event cycle each night. The first REM event occurs approximately 60 minutes after the individual falls asleep and is generally evenly spaced thereafter until the individual wakes up. The first REM event usually lasts about 10 minutes and the length of the REM events generally increases until the last REM event of the night reaches a length of a half hour or so. FIGS. 2a and 2b, 3a and 3b, and 4a and 4b depict the REM cycles of individuals having 4, 5 or 6 REM events per night. FIGS. 2a, 3a and 4a depict the REM cycles of individuals over an eight-hour period, while FIGS. 2b, 3b, and 4b depict 4, 5, 6 REM events per night over a 6-hour sleep period, respectively. In each figure, time extends along the horizontal axis, and the shaded portions of the graphs represent an individual's sleep state. The longer, lower shaded portions 22 represent periods of relatively deeper sleep, while the narrower raised portions represent REM sleep. The numbers above the REM periods represent the duration of the REM event in minutes. The series of numbers immediately below the shaded portions represent the amount of time between REM events as measured from the center of one REM event to the center of the next. The final line of numbers represents the duration of the periods of deep sleep between REM events. As can be seen, the duration of REM events increases as the night wears on, while the duration of the periods of deep sleep remains substantially constant. Thus, taking FIG. 4b as the simplest example, an individual having a four REM event nightly cycle in a 6 hour period and who desires to be awakened after each REM event would require an alarm, or "dream alert" at approximately 65, 140, 234 and 335 minutes after retiring for the evening. The four Dreams Per Night cycle shown in FIGS. 4a and 4b will be the usual period for sleep lengths near the 6 hour range and the 5 or 6 Dreams per Night found near the 8-hour range.

The dream analyzer 18 of the present invention is programmable in the sense that the individual using the device may set the times at which he or she is going to bed at night and getting up in the morning. The user may also set dream alerts to occur at times corresponding to 4, 5, or 6 REM events during the course of the night, calculated from the time the user goes to bed at night and rises in the morning. The dream analyzer 18 is also programmable in the sense that the user may select many of the attributes of the dream alerts to fit his or her own preferences. In an embodiment of the invention the dream alerts comprise flashing LEDs directed toward the sleeping user. The LEDs are arranged in triads of red, green and blue diodes. The user may adjust the color of the flashing LEDs by selecting a single or combination of the red, green and blue diodes. The user may also adjust the overall intensity of the flashing diodes as well as the number duration and length of time between the pulses. Adjusting the intensity of the dream alerts is important in that it is usually more difficult to wake a sleeping person during earlier REM events than during those that take place later, in the sleep period. Thus, if the user wishes to be awakened after early REM events he or she may select a higher intensity dream alert setting for dream alerts that occur early in the night, while reducing the settings for later occurring dream alerts. The user may also program a ramp function wherein the intensity of the flashing diodes gradually decreases and increases over the course of a dream alert.

Figure 5:
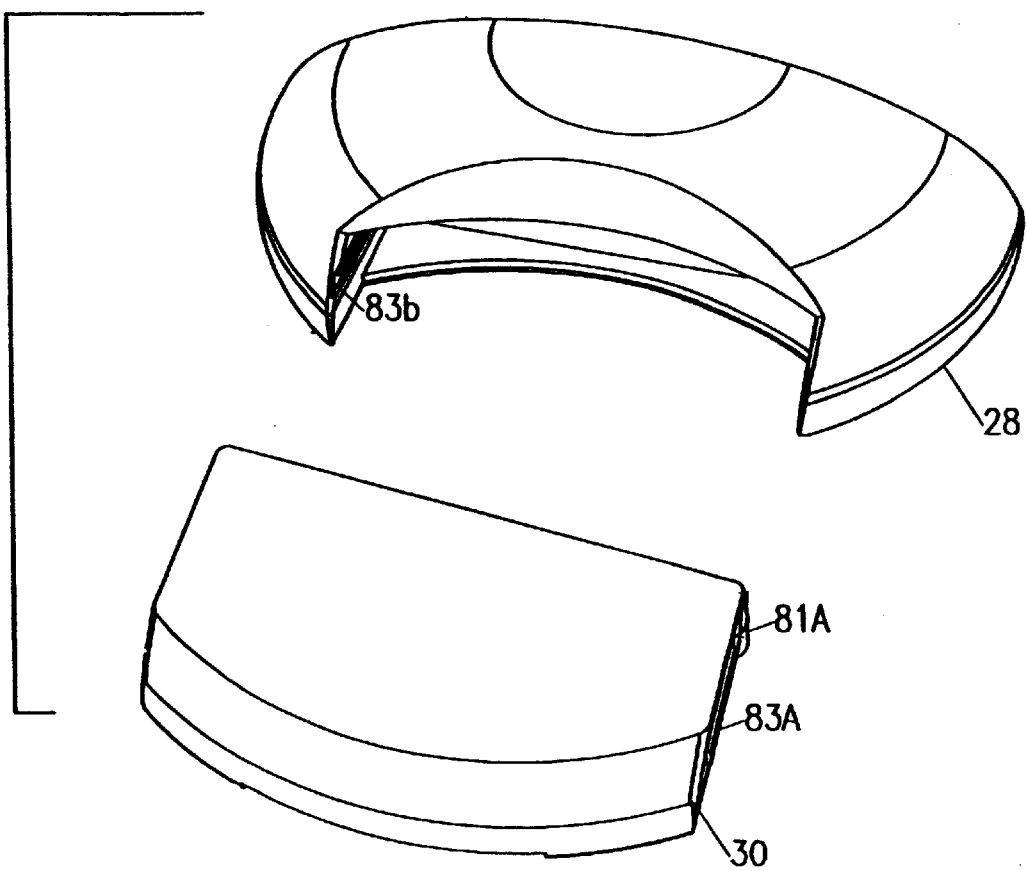
FIG. 5 is a top perspective view of the sleep analyzer apparatus of FIG. 1 as mounted to a wall or the head board of a bed, with an electronic unit withdrawn from a mounting shell.
Figure 6:
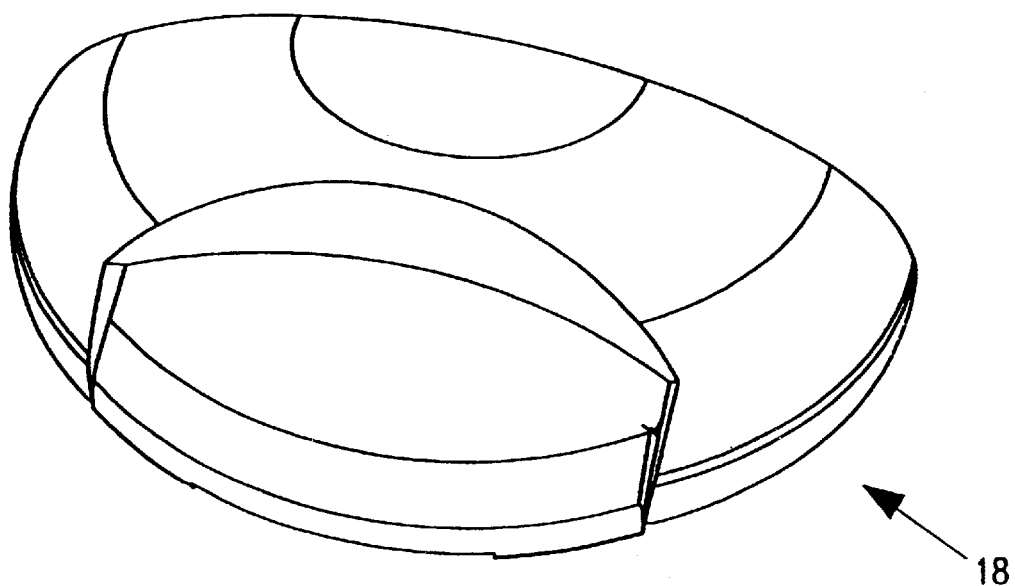
FIG. 6 is a top perspective view of the sleep analyzer of FIG. 1 with the electronic unit properly oriented within the mounting shell.
Figure 7:
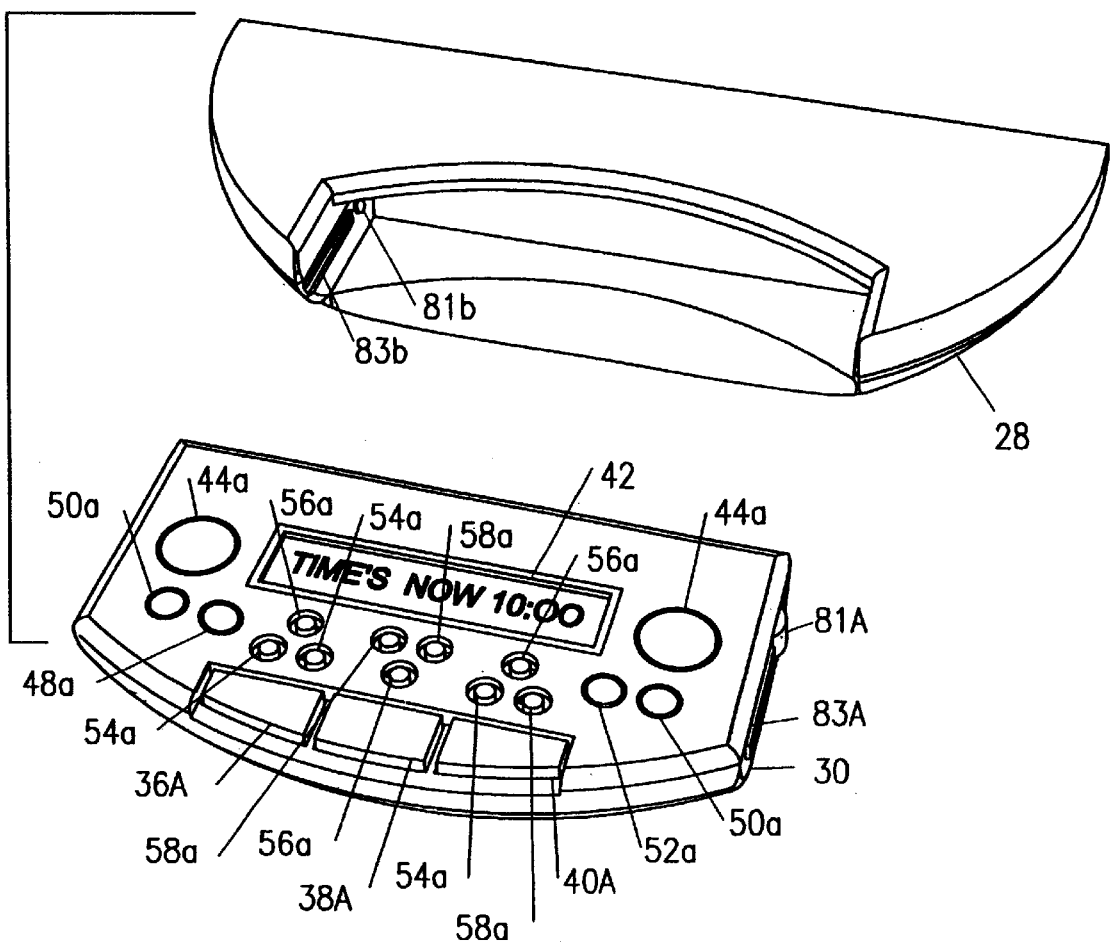
FIG. 7 is a bottom perspective view of the sleep analyzer apparatus of FIG. 1 as mounted to a wall or the head board of a bed, with the electronic unit withdrawn from a mounting shell.
Figure 8:
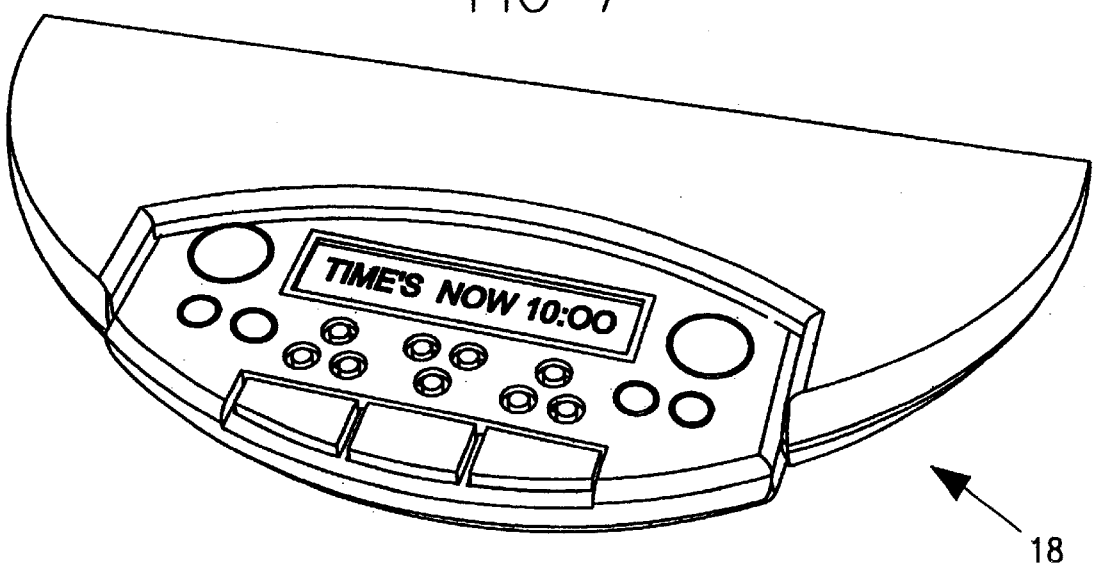
FIG. 8 is a bottom perspective view of the sleep analyzer of FIG. 1 with the electronic unit properly oriented within the mounting shell.

The dream analyzer 18 will now be described with regard to FIGS. 1, and 5–10. FIGS. 5 and 6 show a top perspective view and FIGS. 7 and 8 show a bottom perspective view of the dream analyzer 18 according to an embodiment of the invention. The dream analyzer 18 comprises a mounting shell 28 and a separate removable electronic insert 30 adapted to be slidably mounted within the mounting shell 28. FIGS. 5 and 7 show the electronic unit 30 withdrawn from the mounting shell, and FIGS. 6 and 8 show the electronic unit properly inserted into the mounting shell 28. The view shown in FIG. 8 represents the view that would be seen by the user of the apparatus when lying in bed, similar to that shown in FIG. 1. In this orientation the flat underside of the assembly faces downward and the curved surface faces upward.

The underside of the electronic unit 30 includes a one row 16 character Liquid Crystal Display (LCD) screen 42, such as an Optrex 1617a produced by Optrex America, Inc. of Plymouth Mich. Two speakers, 44a are located on each side of LCD screen 42, and a pair of electret microphones 50a are located immediately adjacent the speakers toward the forward edge of the electronic unit 30. A plurality of LEDs and pushbutton operators are also located on the underside of the electronic unit 30. The pushbuttons include a reset button 48a located to the left of microphone 50a as viewed in FIGS. 7 and 8, and a playback/record button 52 and a trio of pushbuttons comprising a left key press button 36a, a middle key press button 38a and a right key press button 40a. A sequence of display triads is shown below the LCD screen 42. Each display triad comprises a red diode 54a, a green diode 56a and a blue diode 58a. These are preferably HP 15 degree focused view diodes having at least 1500 mll luminosity, but other LEDs or lamps may also be used.

Figure 9:
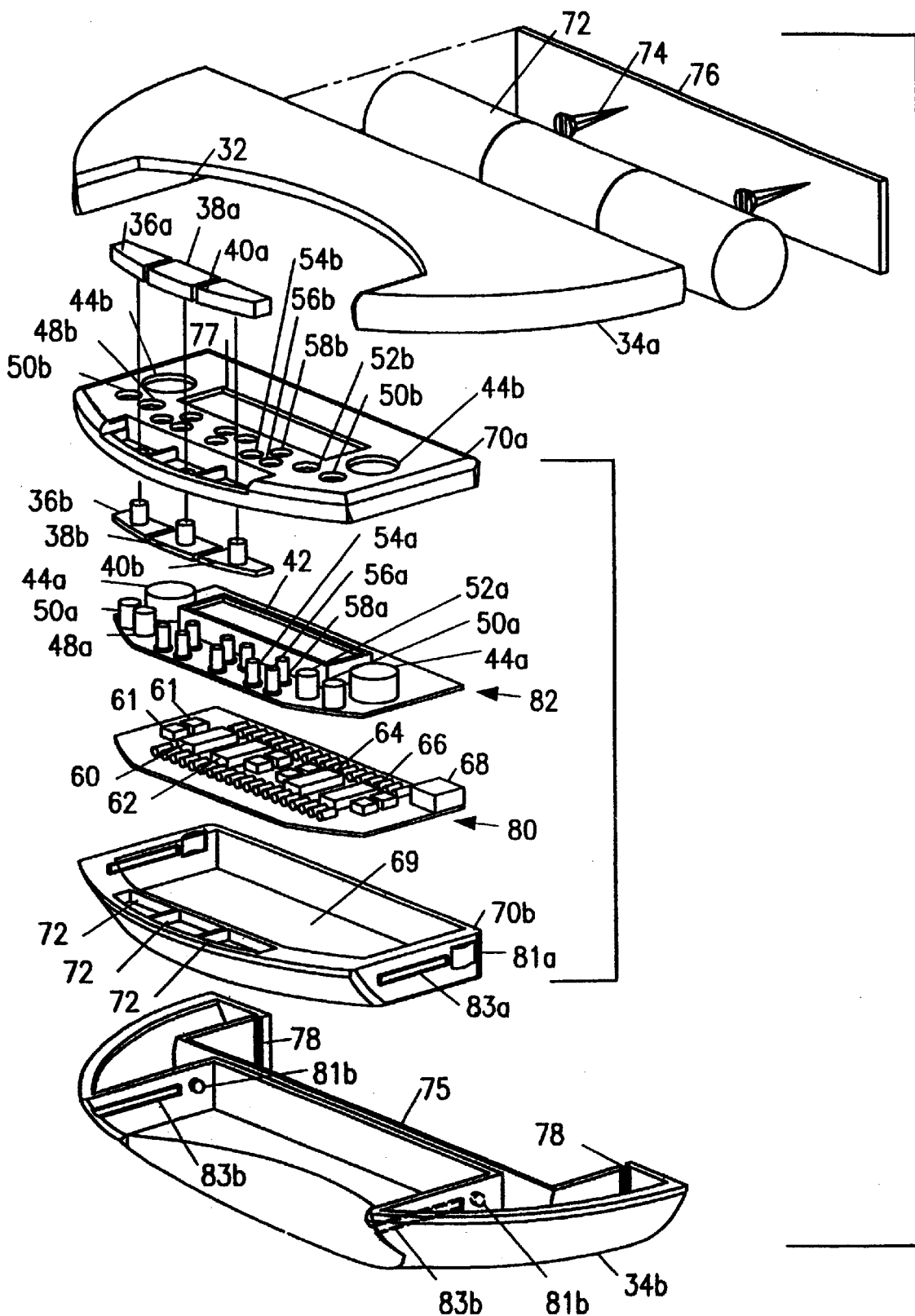
FIG. 9 is an exploded top perspective view of the sleep analyzer apparatus of FIG. 1.
Figure 10:
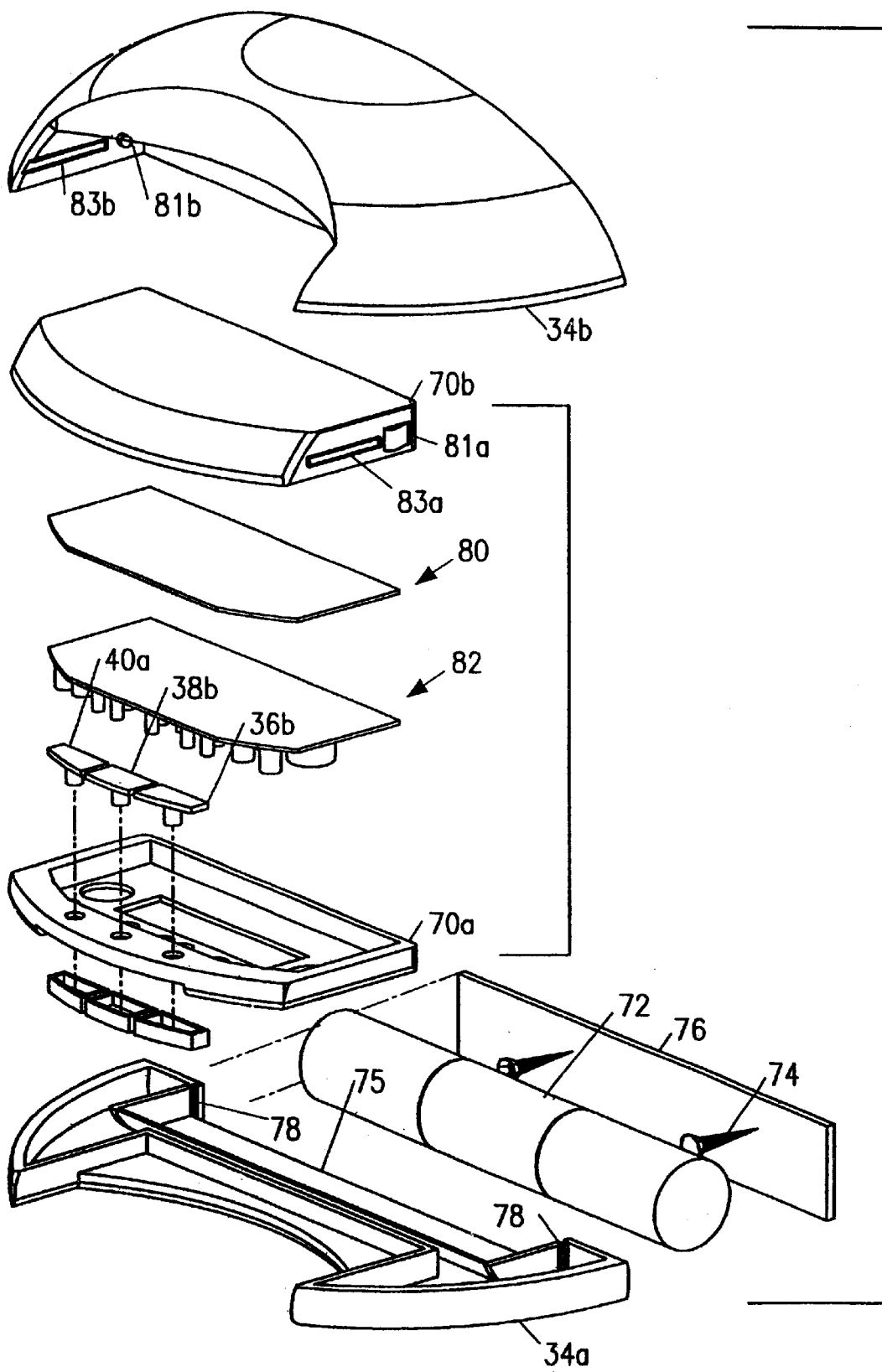
FIG. 10 is an exploded bottom perspective view of the sleep analyzer apparatus of FIG. 1.

FIG. 9 shows an exploded perspective view of the electronic unit 30 and mounting shell 28 in an inverted orientation. FIG. 10 shows the same exploded view of FIG. 9, but from above. Beginning from the top of the apparatus (the bottom of FIG. 9 or the top of FIG. 10) the major assemblies and components of the apparatus are: a mounting shell upper casing 34b; an electronic unit upper casing 70b; a first printed circuit board 80; a second printed circuit board 82; pushbutton switch assemblies 36b, 38b, and 40b; electronic unit bottom casing 70a; pushbutton operators 36a, 38a and 40a; lower mounting shell casing 34a; batteries 73; mounting plate 76 and mounting screws 74.

As best seen in FIGS. 5 and 7, an opening 80 is formed at the forward end of the mounting shell 28. The opening 80 is configured to slidably receive electronic unit 30. A pair of slots 83b are formed along opposite sides of the opening 80 forming tracks for receiving cooperating protrusions 83a formed on the sides of the electronic unit 30. An electrical spring contact 81a is shown on each side of the electronic unit upper casing 70b. The electrical spring contacts 81a align with mating contacts 81b located within the opening 80 of mounting shell 28 at the distal ends of slots 83b. A trickle charger (not shown) connects the batteries 73 with a smaller electronic unit battery 68 mounted on the first printed circuit board 80. When battery 68 is charged, the electronic unit 30 may be removed from the mounting shell 28 without loss of power. The trickle charger is powered by three D size batteries 73 which are contained in a battery compartment 75 formed at the back of the mounting shell 28.

A pair of slots 78 are formed in the upper and lower casings 34a and 34b of the mounting sell. Slots 78 are configured to accept the mounting plate 74 after the mounting plate 76 has been secured to a wall or head board by mounting screws 74. Mounting plate 76 also forms the rear wall of the battery compartment 75.

The removable electronic unit 30 comprises the lower and upper electronic unit casings 70a and 70b. These house the first and second printed circuit boards 80, 82. The LCD screen 42, speakers 44*a*, microphones 52*a*, reset and playback pushbuttons 48*a* and 50*a*, as well as the red green and blue diodes 54*a*, 56*a*, 58*a* of the plurality of display triads are all mounted to the second printed circuit board 82. The first printed circuit board assembly 80 is mounted atop the second printed circuit board assembly 82. A pair of micro controllers 60, 62, are mounted adjacent one another as shown. The first micro controller preferably comprises a PIC16CE625 manufactured by Microchip Technologies Inc., of Itasca Ill., and the second micro controller preferably comprises a PIC16F84 also manufactured by Microchip Technologies, although other similar micro controllers may be readily substituted. Each micro controller is programmed with software that is attached as an appendix to the present specification. Also attached is software for initializing the EEPROMs associated with the micro controllers. A pair of four megahertz crystal oscillators 61 are mounted near the micro controllers 60, 62 for providing clock signals to the micro controllers. Printed circuit board 80 also includes a voice recording/playback chip 66 ISD2575 manufactured by ISD, Inc. of San Jose, Calif., a voice activated switch 64 Rk 990-0085 by Electronic Rainbow Inc. of Indianapolis Ind., and an S/R latch MC14043B manufactured by Motorola of Schaumburg, Ill. As already noted, a small capacity battery 68 is located on the assembly in close proximity to the electrical contact 81*a* on the electronic unit upper casing 70*b*. The battery 68 provides operating power to the components mounted on the first and second printed circuit boards 80, 82 through a +5 volt voltage regulator (not shown).

The left, middle and right key press buttons 36*b* 38*b* and 40*b* are mounted within molded receptacles 72 formed in the upper electronic unit casing 70*b*. When actuated, the pushbutton switches depress spring loaded keypad connections (not shown) which connect circuits mounted on the first printed circuit board 80. Corresponding left middle and right operator covers 36*a*, 38*a* and 40*a* are mounted below the switch assemblies 36*b*, 38*b* and 40*b* and protrude through windows formed in the lower electronic unit casing 70*a* where they are accessible to the user. Similarly, device reset and record/playback pushbuttons 48*a* and 50*a* are accessible through operator access holes 48*b* and 50*b* respectively. Speakers 44*a* are aligned with speaker holes 44*b*, microphones 46*a* align with sound input holes 46*b*, and LEDs 54*a*, 56*a*, and 58*a* align with holes 54*b*, 56*b*, and 58*b*.

Figure 12A:
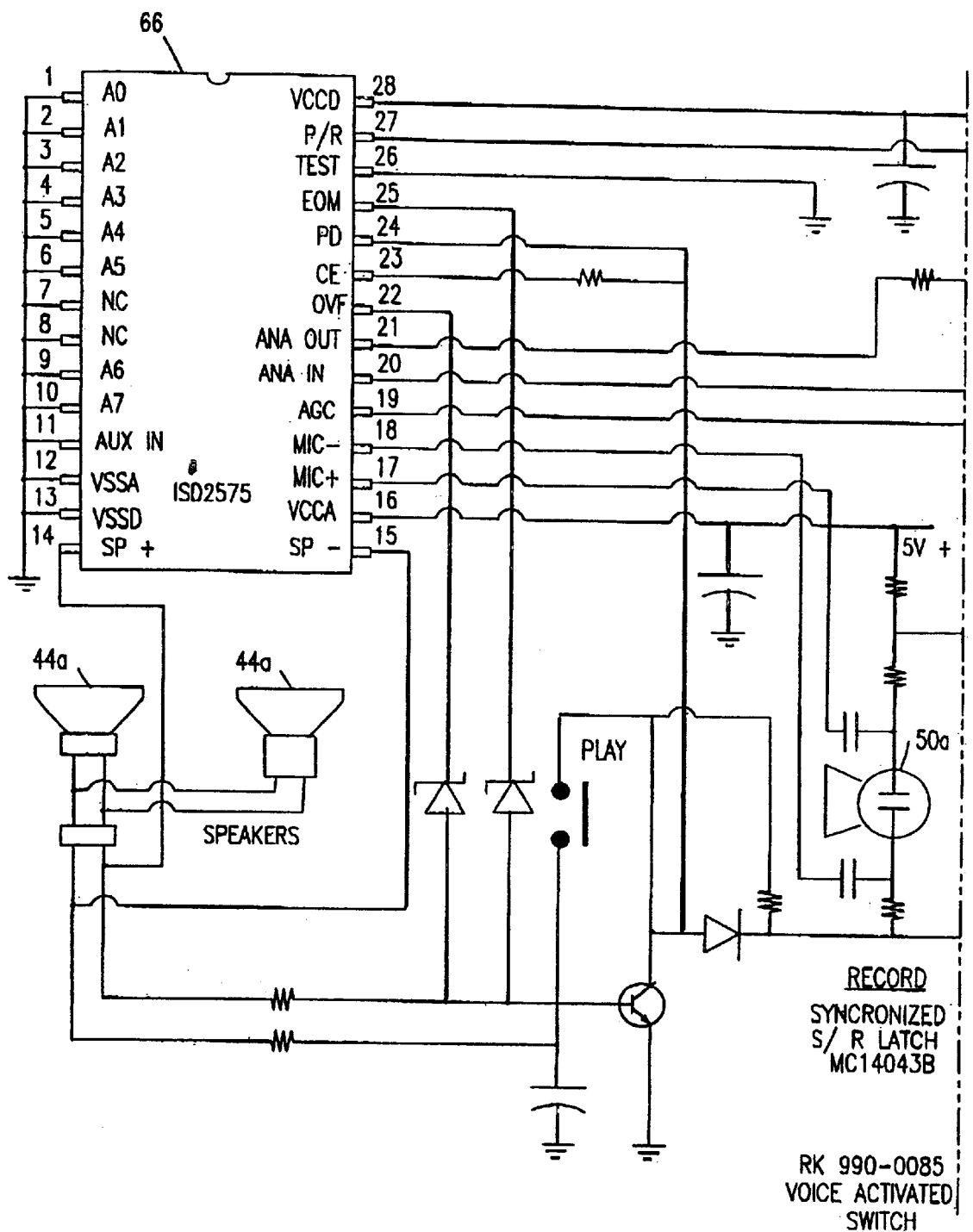
FIGS. 12a, 12b and 12c together form an electrical schematic for the sleep analyzer apparatus.
Figure 12B:
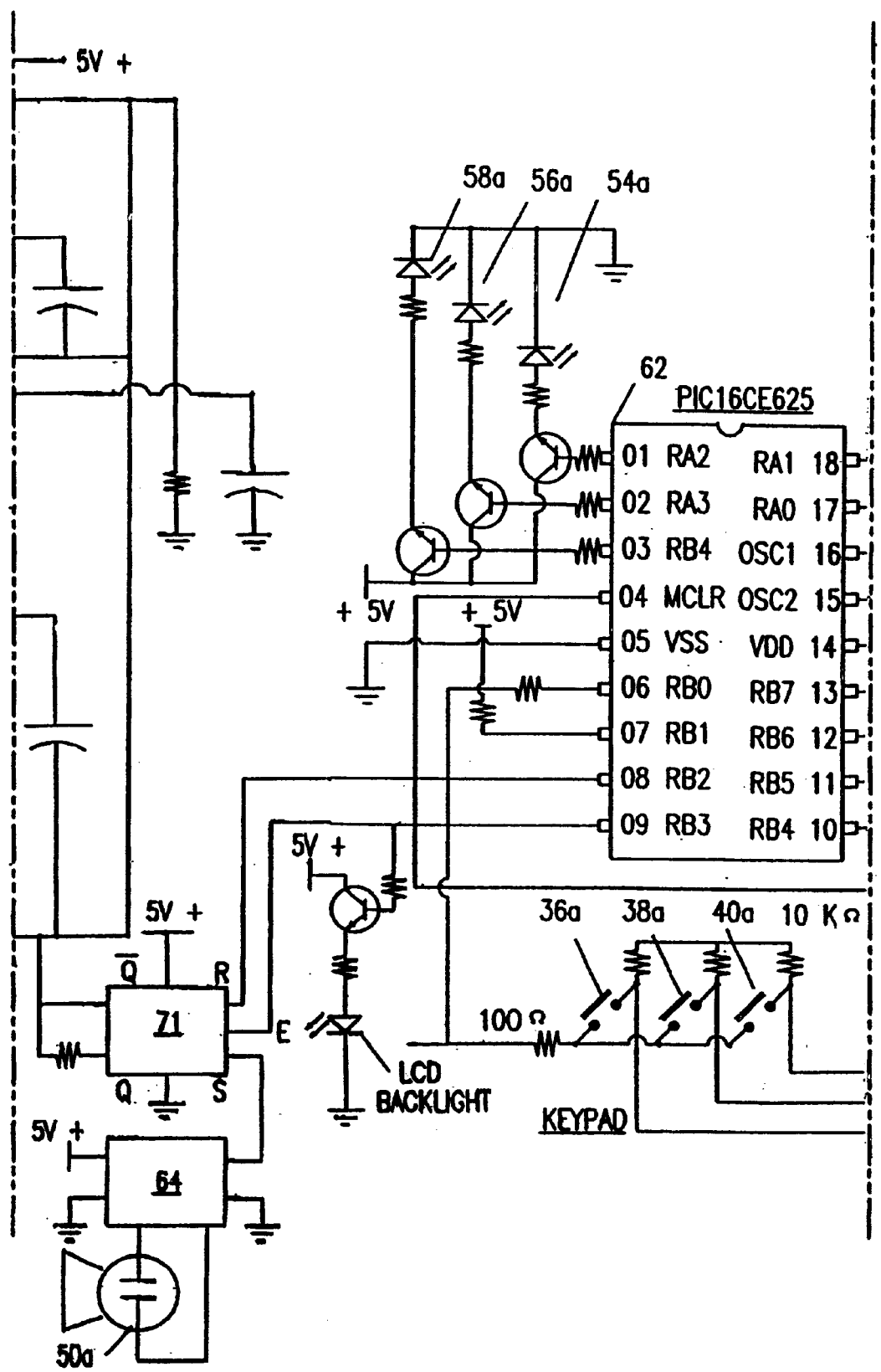
Figure 12C:
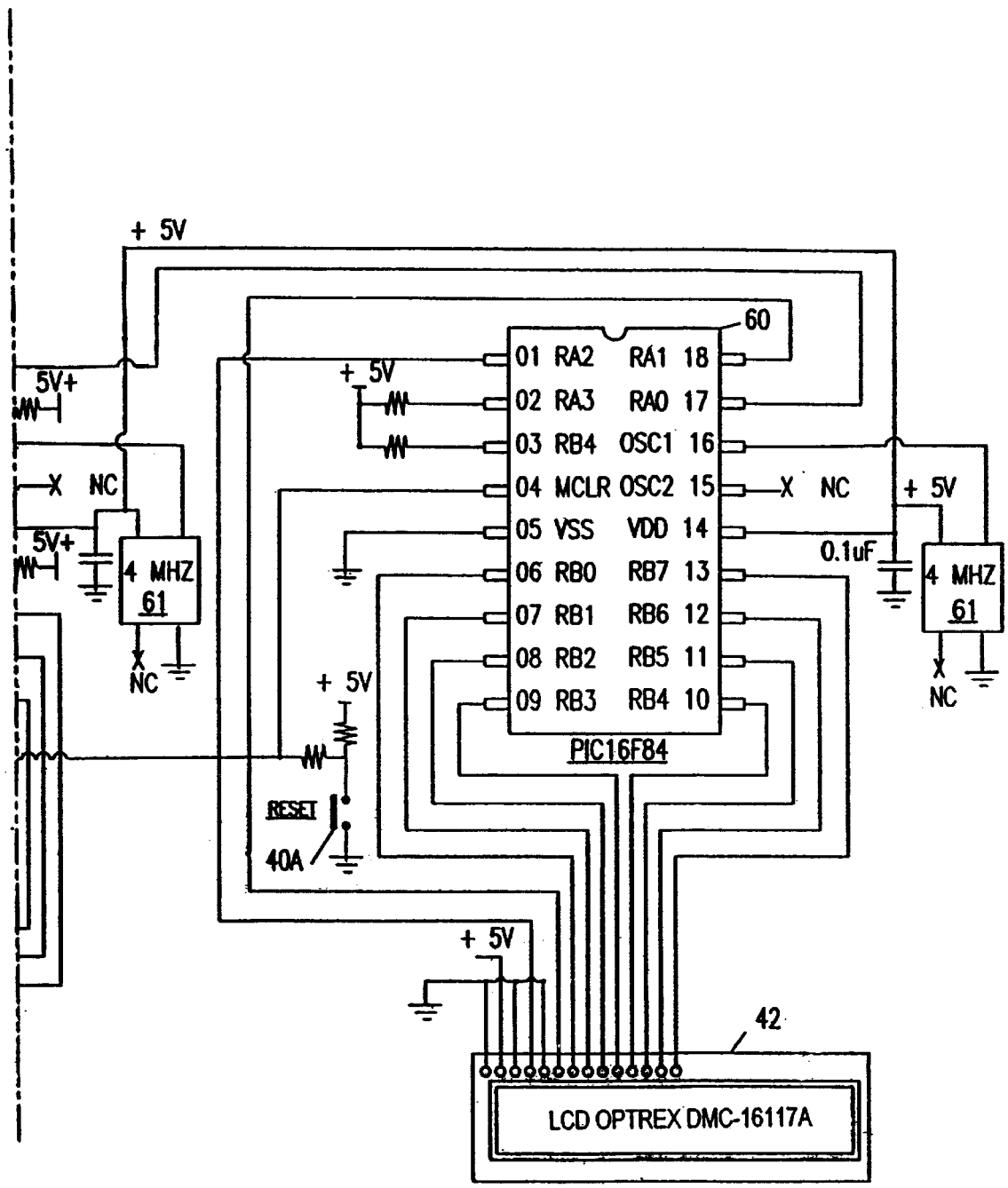

A schematic diagram of an embodiment of the dream analyzer 18 is shown in FIGS. 12*a*, 12*b*, and 12*c*. FIG. 12*a* shows the connections between the voice recording chip 66, speakers 44*a*, and one of the microphones 50*a*. The second microphone 50*b* is shown on FIG. 12*b*, and is connected to the voice activated switch 64. The voice activated switch in turn is input to the S input of the synchronized S/R latch 71. The output from the S/R latch controls the record function of the voice recording/playback chip 66. The play function is controlled by the playback pushbutton 50*a*, all of which are connected as shown. Various biasing, filtering and voltage regulating components are also connected as shown.

The connections to second micro controller 62 are shown in FIG. 12*b*. Oscillator 61 drives the OSC1 input at pin 16 to provide a clock input. Pushbutton switches 36*a*, 38*a*, and 40*a* are connected across RB0, pin 6, and inputs RB4, 5, and 6, pins 10, 11, and 12 respectively. Micro controller 62 drives a backlight for the LCD screen 42 through output RB3, pin 9, and drives the dream alert LEDs 54*a*, 56*a* and 58*a* through outputs RA1, RA3 and RA4, pins 1, 2, and 3. Various biasing resistors and operating voltages are connected to the micro controller 62 as shown.

Turning to FIG. 12*c*, the first micro controller 60 is shown. Oscillator 61 drives the OSCI input, pin 16, to provide a clock input. The primary function of micro controller 60 is to control the LCD screen 42 which is connected to the first micro controller 60 as shown. Micro controller 62 controls the functions of micro controller 60 via a connection between the I/O point RA1, pin 18, on each device. The resent button 40*a* is connected between the CLR input, pin 4, of both micro controllers and ground. By connecting pin 4 to ground, actuation of the reset switch causes the programs running in the micro controllers 60, 62 to be restarted.

In operation, the reset pushbutton initializes the software programs running the micro controllers 60, 62. The user begins the programming process by accepting or updating the current time reported by the device as is denoted by LCD screen 84 on FIG. 11*a*. The user then either alters or accepts the previously stored values for the length of time to be spent asleep as is shown by the LCD screen 86. The current time and total sleep time values can be updated by pressing the middle 144 or right 146 programming pushbuttons (38*a*, 40*a* of FIG. 7) The middle key press 144 adjusts the time down and the right key press adjusts the time up in one minute increments. The device then calculates the time of all REM events for all Dreams per Night cycles. As the three different cycles all begin and end at the same time for a given sleep length period, a total of eleven REM periods are calculated for any given current time and any given sleep length period. These are intervals 26 noted on FIGS. 2*a*, 2*b*, 3*a*, 3*b*, 4*a* and 4*c*. These calculations are stored and made available for review by the user who may then set or clear any or all of the Alerts based on the calculations as the user may select.

This is done when accessing the LCD screens 88, 90, 92, 94, 96 and 98. These screens are automatically sequentially displayed as indicated by diamond blocks 152, unless one to the left middle or right programming buttons is pressed as indicated by diamond blocks 142, 144 or 146. Screens 88, 92 and 96 show the location of the user in the program sequence of 4, 5 or 6 Dreams per Night cycles. Screens 90, 94 and 98 each report the number of Alerts for their respective Dreams per Night cycle. The user may choose to allow the program to automatically sequence through the screens 90 to 98 without interruption, thereby accepting the settings of previous use as the settings of the present use. This will be the usual mode as users empirically arrive at their individual settings with the use of the dream analyzer 18 over a period of time.

Should the user care to review the time of alerts, this may be done by calling up a second level of screens. This is done at the screen locations 90, 94 and 98 by pressing the left key button 142. With the continued pressing of left key button 142, the Dreams per Night cycle invoked will only report the time of each of its alerts and whether each is set or is clear. At screen locations 100, 104, 106, 110 and 112, pressing the middle button 144 will set an alert at the time shown and pressing 146 will clear an alert so that the programmed alert will not occur at the time shown. Pressing the left button 142 is then required to store the new setting and continue the programming sequence.

The last alert setting for the 4 Dreams per Night Cycle is the fourth screen for the alerts screen 108. Pressing the left key button 142 from this screen returns to screen 92. Similarly, the last screen for the 5 Dreams per Night alert settings is screen 110. From there pressing the left key button 142 returns the program to screen 96. Pressing the left key button from the last alert setting for the 6 Dreams per Night cycle, screen 112 returns the program to the operations screen 190 and the Lab displays the current time in minutes until a set alert time activates the user's programmed alert variables.

These variables are accessed from the screen locations noted above. The screen 102, which alternates with each alert setting, screen 100 through 112, will invoke all the settings for an alert if the middle button 144 or the right button 146 is pressed while this screen is displayed. The screens 114, 118, 122, 126, 130, 134 and 138 display each separate variable but without its stored value. Pressing the middle button 144 or the right button 146 will rapidly cycle the user through the variables. A left button press 142 will display the stored value of a particular variable. This allows a user to focus on a variable for an alert setting, which is of particular interest. The value for any variable may be increased by pressing the right button 146 and decreased by pressing the middle button 144 as is shown by the boxes 190 and 192.

If the sequence of screens 116, 120, 124, 128, 132, 136 and 140 is entered at any screen other than screen 116, however, the entire sequence must then be reviewed beginning at the flashes/event screen 116. This review of all variables for an alert event allows the user to consider the entire effect on the alert with just a single changed variable as the new focus.

The alerts are divided into early middle and late categories. In the four dream cycle, the first REM event is classified as early, the middle two are classified as middle, and the last is classified as late. For the five dream cycle the first REM event is early, the second two are middle, and the last two are late. Finally, for the six dream cycle the first two REM events are early, the second two are middle, and the last two are late. The beginning, middle and ending dream alerts for each cycle share a separate set of stored values for each variable. Thus the number of flashes, screen 116; the intensity of the flashes, screen 120; the length of time the LEDS are on, screen 124; the length of time the LEDS are off, screen 132; the ramping up and down of the intensity of a series of flashes, screen 132; and the color of the flashes, screen 136 may have three different and separate sets of user values. This will allow a user to store varying settings for the alerts for the early, middle or last part of the sleeping period. Such flexibility will allow the user greater control over awakenings by cutting values to the barely noticeable for some part of the night while holding other values constant as a control group in dream awakening experimentation.

The final screen in the series described above, screen 140, is a test screen for the alerts. A user will press the right button 146 to toggle between running the test or not running the test. When running the test, the dream analyzer 18 will pass time at 4 minutes per second until a set alert time and will then activate the alert at its actual rate. It will continue to do so until the reset button is pressed, clearing the test. If no further user action takes place the program will continue automatically to the first operations screen, screen 190. It will then display the current time until set alert times activate the required values which were earlier programmed.

With the activation of an alert, a back light for the LCD 204 in FIG. 12c is lit and the voice activated switch is enabled. These remain enabled for several minutes following the end of an alert. Because a dream will be lost if a sleeper moves before mentally reviewing the dream, the voice-activated switch enables the voice record chip so that statements about the dream may be recorded without requiring the user to move. Also not moving will enable the user to quickly fall back into NON-REM slumber after such notes are taken. On arising the following morning, the manual playback button 50a will cause the record/playback chip to replay the comments recorded during the night, allowing the user to remember the dream that would otherwise probably have been forgotten.

A more detailed description of the flowchart depicted in FIGS. 11a, 11b, 11c and 11d will now be given. The four vertical columns of numbered boxes represent four levels or series of LCD display screens. A series of rounded Operation boxes 190, 192, 194, 196, 198, 200 and 202 is located on FIG. 11c at the bottom of the first column. These show the sequence of programmed operations once user input has been completed.

From the top of the first column, the sequence of boxes 84, 86, 88, 90, 92, 94, 96 and 98 show the LCD display screen input pages in which program settings are entered for setting the times for dream alerts, and setting the user preferences for the alerts as well. An "X" is shown as a placeholder of a decimal value that would actually appear on the screen as the result of actual user input or device operation. This first column of the LCD screen input pages sequentially shows the user the number of alerts that are currently set for the 4 Dreams per Night Cycle, the 5 Dreams per Night Cycle and the 6 Dreams per Night Cycle. The times at which the dream alerts will occur are automatically calculated based on "Time Now" setting of box 84, and the "Total Sleep" setting of box 86. These are values are the values that had been stored from the previous use of the dream analyzer.

The diamond boxes 142, 144 and 146 respectively represent the left, middle and right key press buttons 36a, 38a and 40a shown in FIG. 7. Boxes 148 and 150 show the current time setting increasing or decreasing in one minute increments when the right or middle keys are depressed. Pressing the left key as depicted by diamond box 142 advances the LCD display to the next programming page 86.

Diamond boxes 152 represent the automatic sequencing of the programming pages. If no buttons are pressed during this sequence, the LCD screen will quickly step through all of the settings currently stored in the dream analyzer 18. Each page will be displayed for approximately three second to allow the user to make changes if desired, otherwise the display advances to the next page. A key press of the left button 142 will stop the automatic progression of LCD screen displays and will then restart the sequence following increase, decrease or no change in the displayed value of a screen by the user.

Box 90 will report the number of alerts or events that have been set for the 4 Dreams per Night cycle. Box 94 will report the number set for the 5 Dreams per Night cycle and Box 98 the number set for the 6 Dreams per Night Cycle.

Figure 11A:
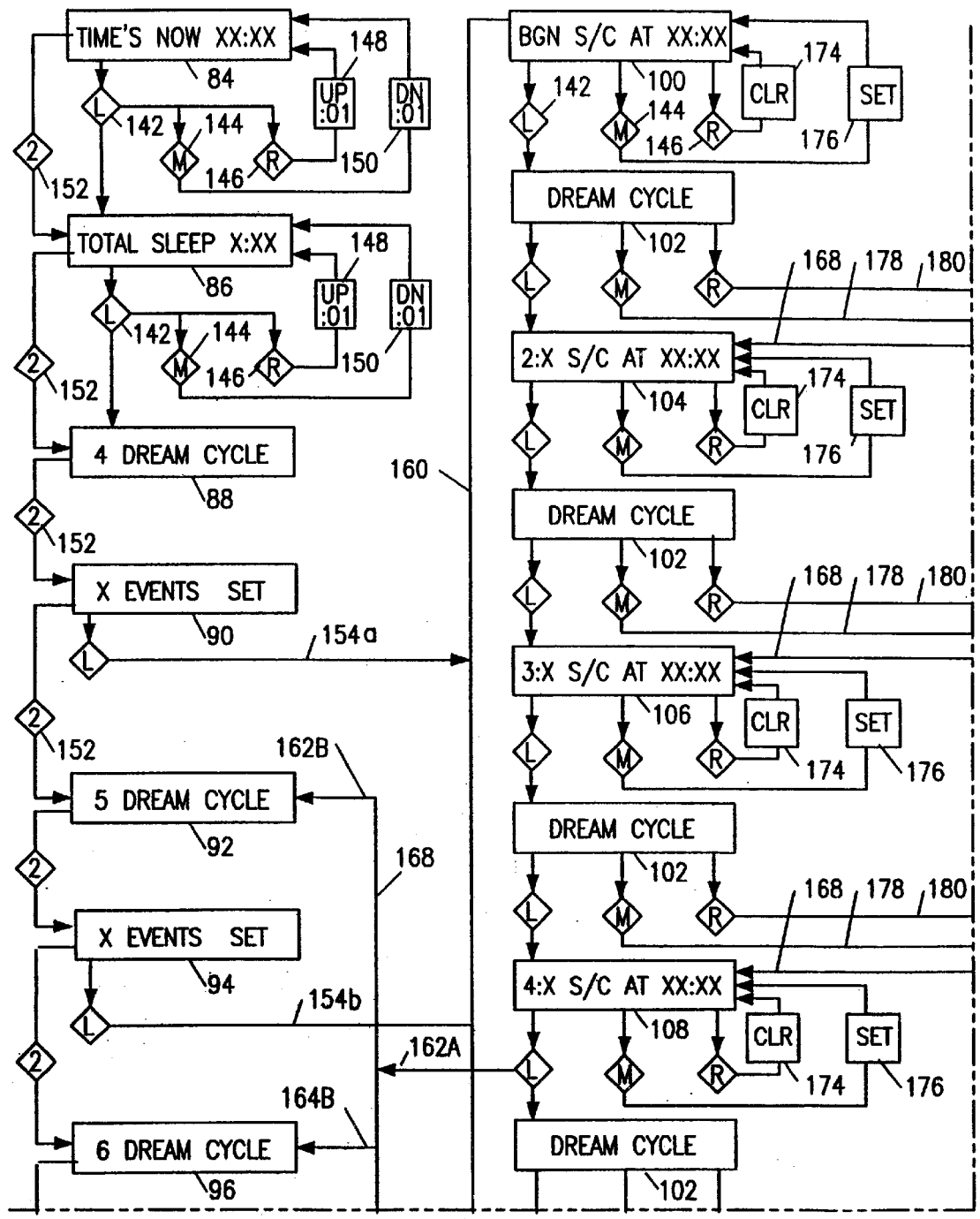
FIGS. 11a, 11b, 11c and 11d together are an operational flowchart illustrating the Program Interface as the user sets the times and alert variables for the sleep analyzer apparatus' operations.
Figure 11B:
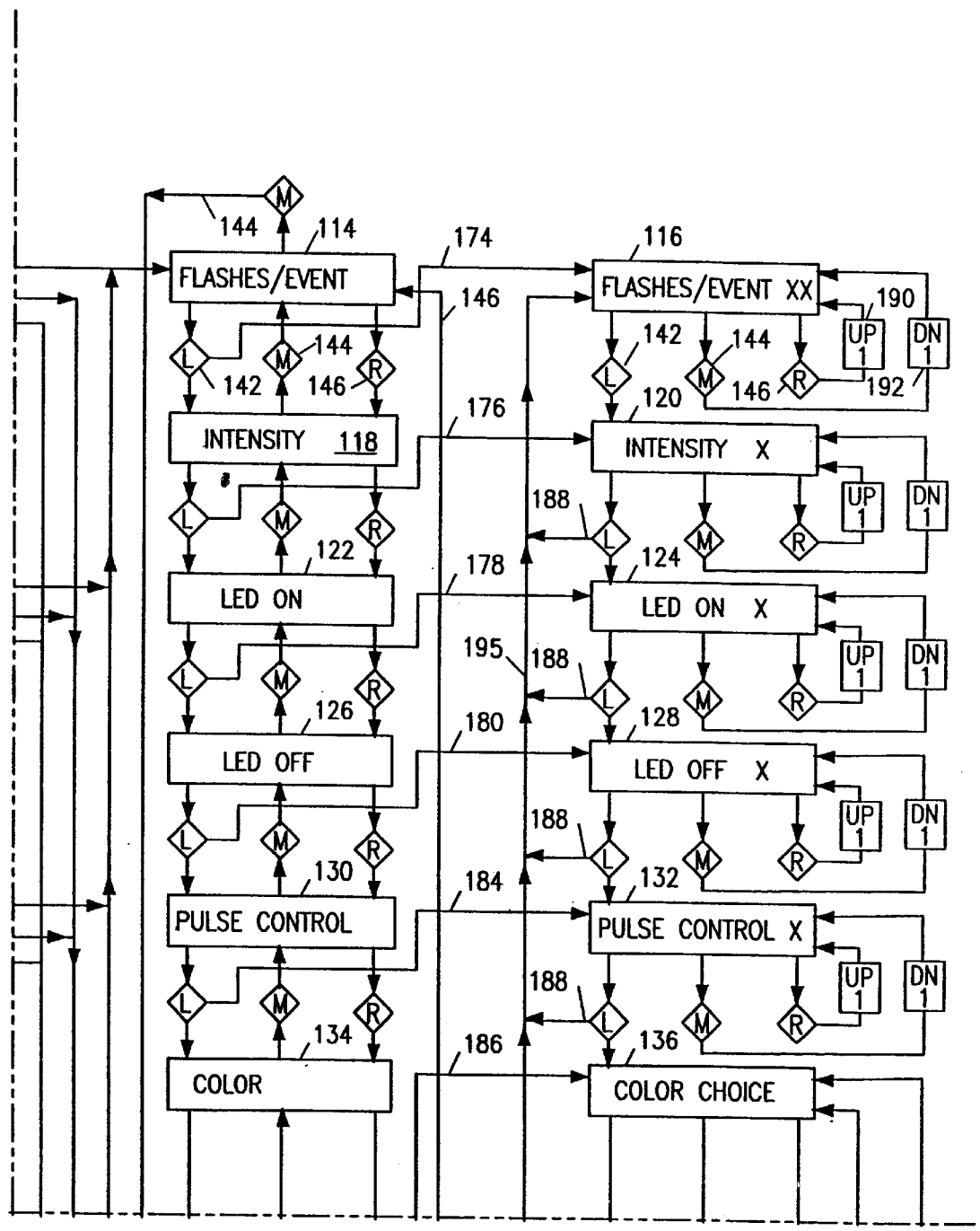
Figure 11C:
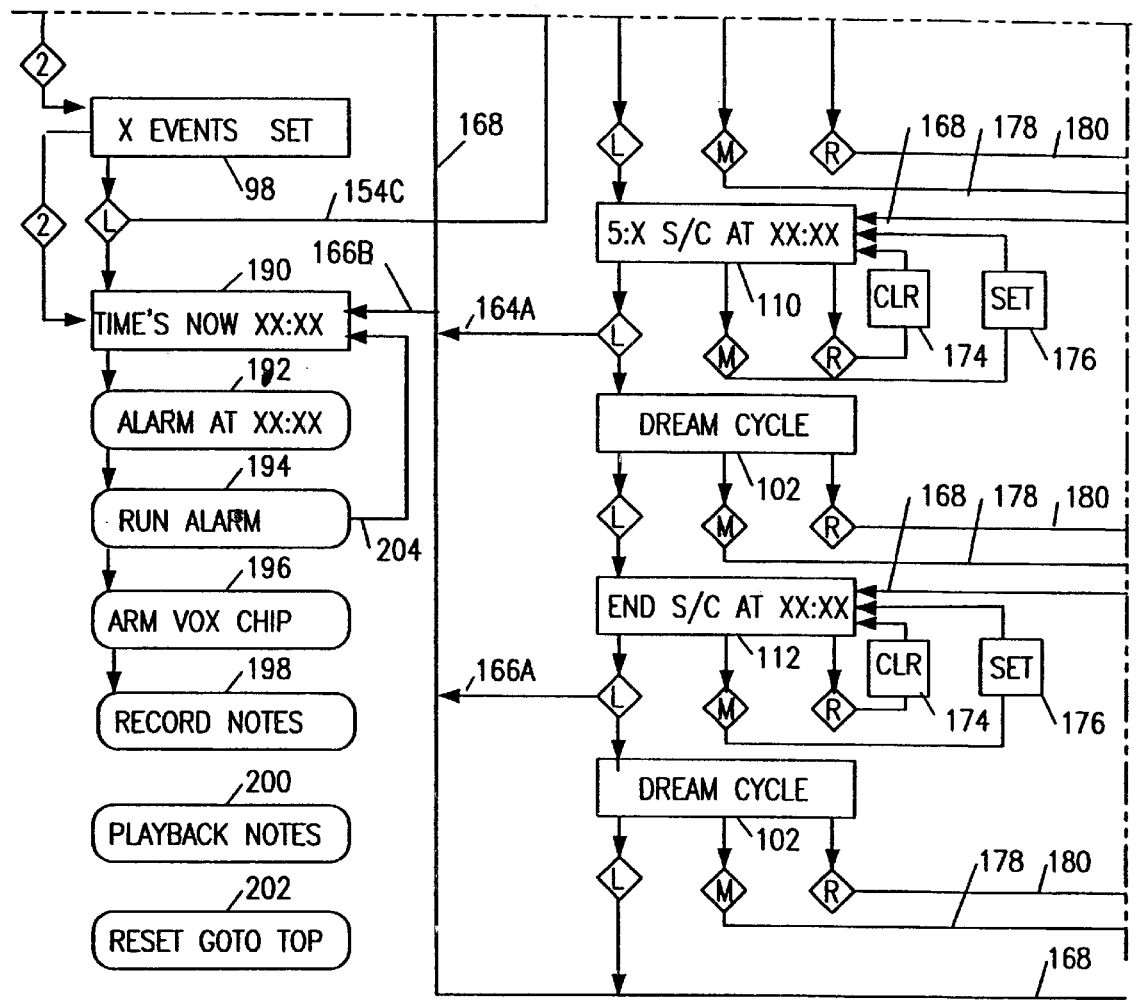
Figure 11D:
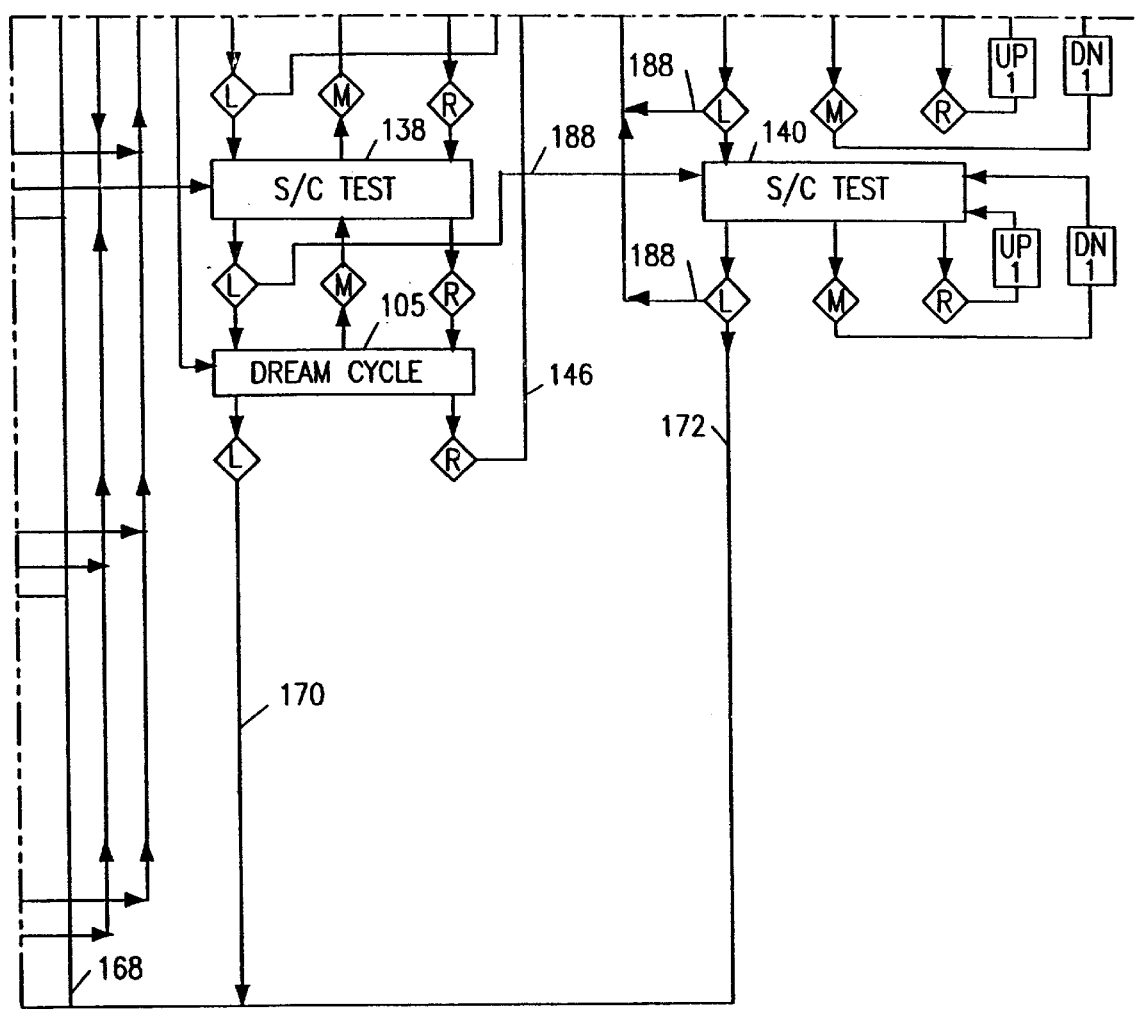

In FIGS. 11a and 11c, routes 154a, 154b and 154c connect with route 160 and show the connection of the first column, series or sequence of LCD boxes with those of the second column, level or series. The route 162a connects through route 168 to route 162b as does route 164a with route 164b and route 166a with route 166b to show three separate connections of the second column back to the first column. These connections back to the first column occur at the 4$^{th}$, 5$^{th}$ and 6$^{th}$ alerts respectively, depending on whether the 4 DREAM CYCLE, 5 DREAM CYCLE or 6 DREAM CYCLE is being programmed.

The second column or sequence of boxes show LCD display screens 100, 104, 106, 108, 110 and 112, all of which alternate with LCD screen 102. These screens show an additional placeholder "S/C" that is either "SET" or "CLR" (clear) depending on which is selected by the user. Set and Clear are selected by depressing the middle key or the right key as shown. Thus, each dream alert for each dreams per night cycle (i. e. 4, 5, or 6 dreams per night) can be set cleared.

Continued pressing the left key 142 indicates progression through all screens with no change in alert status.

The alternating LCD display screen 102 shows route 178 and route 180 connecting the second column or level of LCD display screens with a third level of screens. These connections allow characteristics of the dream alert associated with each dream cycle to be independently set. Pressing the middle key 144 at the dream cycle pate 102 will connect to the top LCD display screen 114 and pressing the right key 146 will connect to the bottom Dream Cycle page 105 located at the bottom of the third column. For this third column of screens, a right key press 146 will continue the progression of screens from top to bottom while a middle key 144 press will continue the progression from bottom to top.

A user may quickly select a particular variable shown in boxes 114, 118, 122, 126, 130, 134 and 138 in the third column or level of screens. A left key press will then indicate the current value for the value as indicated in the fourth column or level of LCD screen displays. Boxes 190 and 192 show that an increase or decrease in value may then be made by either a right key press 146 (increase) or a middle key press 144 (decrease). A left key press 142 will change the displayed page to the next variable dream alert variable.

If the user has entered the fourth column or level of display at any screen other than screen 116, a value entered for that screen will immediately thereafter return the sequence to screen 116, This is indicated by the common routes 188. The left key press 142 will in all instances then proceed through the fourth level of screens 116, 120, 124, 128, 132, 136 and 140. These screens must all be reviewed each time this level is entered from the third level of LCD screens.

LCD screen display 140 shows SET TEST or CLR TEST which may be changed or not by the user before the fourth level returns on route 172 connecting to route 168 to box 92, box 96 or box 190 in the first column or level of LCD screen displays. If the user makes no selection, the default value is CLR TEST.

Progression through the four columns will finally end the user program input and arrive at the LCD screen 84*b* at the bottom of the first column in FIG. 11*c*. If the user has entered SET TEST in box 140, the run time box will proceed at the rate of 3 minutes per second and will run the alert functions in actual programmed time. If the user has entered, or has left unaltered screen 140 CLR TEST from the previous use, the run time screen 190 will proceed at usual clock time.

Box 192 indicates alerts or alarms. Box 194 indicates these will run at the programmed time if they have been set by the user or bypassed if they have not been set.

If the alarm is set, box 196 indicates that the voice activation switch has been set. This will stay active for a short while to capture any notes voiced by the awakened user. If the user is not awakened, the chip will not record but will await the next alarm for possible recording.

Box 200 shows that the manual playback of the record/playback chip may take place when the user desires.

Box 202 indicates that the manual reset button will start the programming of the device at box 84*a* at the top left of FIG. 11*a*.

Figure 13:
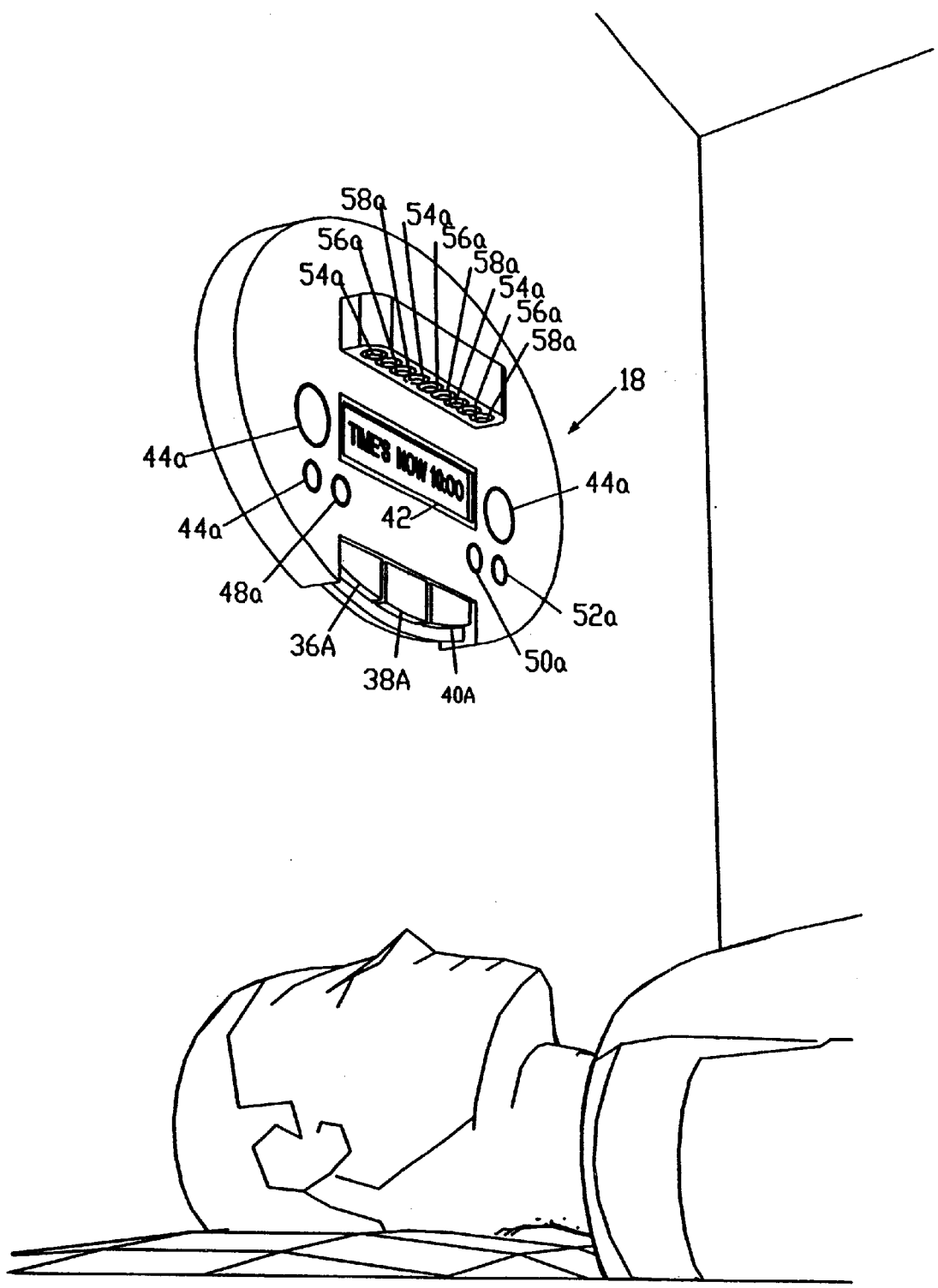
FIG. 13 is a perspective view of an alternative embodiment of the invention in use.

FIG. 13 shows an alternative embodiment of the invention at 216. Assembly 216 shows the device as a single casing. It provides the same features shown in the preferred embodiment. The red diodes 54*a*, the green diodes 56*a* and the blue diodes 58*a* are shown in the same orientation as the preferred embodiment. The speakers 44*a*, the electret microphones 46*a* and 52*a*, the LCD screen 42, the key press buttons 36*a*, 38*a* and 40*a*, the Sound Playback button 50*a* and the Device Reset button 48*a* are all at right angles to the orientation of the preferred embodiment.

All features and operations of the preferred embodiment are the same as those of the alternative embodiment. The significant differences between the two are the removable insert casing 30 of FIG. 7. This is smaller than the assembly 216 of FIG. 13 and is easy to remove from its normal placement. Additionally, it shows its LCD screen with backup light for the user during its active alert times so that the user need not move to check on the status of the device. Also, the flat horizontal lower surface of the preferred embodiment more easily rests upon a bed-stand headboard.

Assembly 216 may have the advantage of lower cost through the use of less casing material. Also, the assembly may have the advantage of familiarity in that it more nearly appears as a picture mounted to the wall.

While my above descriptions contain many specificities, those should not be construed as limitations on the scope of the invention, but rather as exemplification of one preferred embodiment thereof. Many other variations are possible. For example: cell phone, personal digital assistant and hand-held electronic game operations offer subtle possibility.

Accordingly, the scope of the invention should be determined not by the embodiments illustrated, but by the appended claims and their legal equivalents.

APPENDIX

Pic16f84.hex Program
The Object Code for the Pic16f84 is to be loaded
into the chip and will control the LCD display

```
:100000008B294430B3005230B4004530B500413044
:10001000B6004D30B7002030B8004330B900593039
:10002000BA004330BB004C30BC004530BD00080076
:100030005430B0004930B1004D30B2004530B3000B
:1000400006030B4005330B5004E30B7004E30B800C8
:100050005730B9003A30BD0008005430B0004E307E
:10006000B1005430B2004130B3004C30B4005330D2
:10007000B6004C30B7004530B8004530B9005030BC
:10008000BA003A30BD0008004530B3005630B40025
:100090004530B5004E30B6005430B7005330B8008C
:1000A0002030B9002030BA005330BB004530BC00CE
:1000B0005430BD0008004130B8005430B900203041
:1000C000BA003A30BD0008004230B0004730B100FD
:1000D0004E30B20008003230B0003A30B1000800B3
:1000E0003330B0003A30B10008003430B0003A305C
:1000F000B10008003530B0003A30B10008003430AB
:10010000B20008003530B20008003630B20008F06
:100110004530B0004E30B10044430B20008004330EA
:10012000B4004C30B5005230B60008005330B40073
:100130004530B5005430B60008002030B4002030FF
:100140000B5002030B60008004530B0004E30B10098
:100150004430B20008004630B0004030B1004130AD
:10016000B2005330B3004830B4004530B5005330CE
:10017000B6002F30B7004530B8005630B9004530D2
:10018000BA004E30BB005430BC0008004C30B00008
:100190004530B1004430B2004930B4004E30B500B3
:1001A0005430B6004530B7004E30B8005330B90077
:1001B0004930BA005430BB005930B000080040300
:1001C000B00004530B1004430B2004E30B4004E3082
:1001D000B5005430B7004930B8004D30B900453053
:1001E000BA0008004C30B0004530B1004430B200D5
:1001F0004F30B4004630B5004630B6005430B80039
:10020000493089004D30BA004530BB0008005030CD
:10021000B00005530B1004C30B2005330B30045301F
:10022000B4004330B6004E30B7004E30B800543001
:10023000B9005230BA004E30BB004C30BC0008004F
:100240004330B0004F30B1004C30B2004F30B300FB
:10025000052308B40008005430B8004530B900533073
:10026000BA005430BB0008005230B6004530B70029
```

APPENDIX-continued

```
:100270004430B80008005930B6004530B7004C3063
:10028000B8004C30B9004E30BA005730BB000800FE
:100290004730B6005230B7004530B8004530B9009D
:1002A0004E30BA0008004230B6004C30B70055302E
:1002B000B8004530B9002D30BA004730BB0052308D
:1002C000BC004530BD004530BE004E30BE000800C8
:1002D0004230B6004C30B7005530B8004530B90058
:1002E00008004D30B6004130B7004730B800453007
:1002F000B9004E30BA005430BB004130BC00080099
:100300005730B6004830B7004930B8005430B90013
:1003100004530BA0008008316013085000030860A1
:10032000831200308600851005118511051278238F
:100330008323C0238D239B239601CB23160899008A
:100340009601CB2316089A009601CB2316089B0032
:10035000190800AC03199C291908013C031989223A
:100360001908023C031997221908033C0319D222E9
:100370001908043C0319D6221908053C0319DA228E
:100380001908063C0319DE221908073C0319E2226A
:1003900019080803C031916221908093C0319EA2246
:1003A00019080A3C03198B2919080B3C03193B2235
:1003B0001908003C03195B2219080D3C0319F322A0
:1003C00019080E3C0319042319080F3C03192023B4
:1003D0001908103C031924231908113C03199B2206
:1003E0001908123C0319F221908133C0319AB2268
:1003F0001908143C0319AF221908153C0319B3223C
:100400001908163C0319B6221908173C0319BF2214
:100410001908183C031902221908193C03190522EE
:100420001908A13C031908221908B13C03190B22CE
:100430001908103C0319A32219081D3C0319A72203
:100440001908F3C0319F021908203C0319B922AF
:100450001908213C0319B0221908223C03197D22EA
:100460001908283C031993221908009293130840070
:100470001A0880&00800782320211A08003C03197C
:1004800080211A08013C031934211A08023C03197F
:100490003B211A08033C031948211A08043C03199C
:1004A00053211A080530031968211A08063C031950
:1004B00071219B23080078231A08C0300319D222DB
:1004C0001A08013C0319D6221A08023C0319DA2241
:1004D0001A08033C0319DE221A08043C0319E2221D
:1004E0001A08053C0319E6221A08063C0319EA22F9
:1004F0001A08073C0319972208007823182092323
:100500008000078231820203BD009B2308009B237F
:100510008000078232D20932308007823220203DED
:100520000BD009B2308007823442093B2308007823E8
:100530001209B2308064205B209B2308007F2070
:100540005B209B2308008F202B219B2308009620F3
:100550002B219B2308008220B5B209B230800852001
:100560008B209B23080088F209B23080096209B2361
:100570008009D209B2308007B239B2308006B2004
:100580008009B2308007020B9B230B007520B9B230B004
:10059007A209B2308008820B5B20B9B2300B00A420E4E
:1005A00058B2008007823AB209B2308007823C6201B
:1005B0009B23080007823DF209B2308007823F22068
:1005C0009B2308007823072198B2308007823202100
:1005D0009B2308007823B2219B2308007823B234F
:1005E0000009B2399C29B1083F3C0319472B1B0839
:1005F00003F3C031919C231B083D3C0319562B1B08A2
:100600003C3C0319602308001B083F3C031947823A7
:100610001B083E3C03194C231B083D3C0319512386
:1006200001B083C3C03195B231B0831300319652361
:1006300000800081A08282398230000A086A230800C8
:1006400001A082B2398230001A083223B8230B0037
:100650008C003923080808C003E230B8BA00D08D8
:100660009B00080008C003E230E08BF0000D0B8E0034
:1006700000800000C080F396D238E000B00000C080F3994
:1006800006D238E000C0E0F396D238D008001D2385
:100690000B08BF0009B2308001D230E08BE0009B23EB
:1006A0008001D230E08BC0009B2308001D230E0814
:1006B000BD009B2308001D230E08B9230B00E0
:1006C0001D230E08BC0009B2308001D230E08B1004B
:1006D009B2308008C03923B08008F00093C031C71
:1006E0007227B752B0F08373E08000F08300E0800AC
:1006F001030940303084002030800009400B812B27
:1007000000800840A7D2B4830B0004530B1004C30E1
:100710008B200B3004F30B40008008510511BB23B0
:1007200003380860C06230C3D8600C6230638600B8B
:100730000C623C02308008510511BB23830860026
:10074000C623051BBB23030360B4000B0886000C236D
:1007500000373004020319B2B3F3004020319008009A
```

APPENDIX-continued

```
:10076000840AA52B0511BB23C0308600C6230515BE
:10077000840ABB23A52B2A309400940BBD2B0800C0
:10078000029309500BB23950BC22B0800851400006F
:100790000851DBB2308008B128B1381016400831624
:1007A000D830810083120830970000518D52B80308F
:1007B00081000B110B1DDA2B0518D52B81010B11B4
:1007C0000B1DE02B0B110508090090D970B4C
:0807D000E02B0B1DE92B0800D2
:00000001FF
```

Pic16ce625.hex Program
The Object Code for the Pic16ce625 which is to be
loaded into the chip or emulator program memory.

```
:10000000C1288430F5008316472880300E28F3007D
:1000100087300E28F3008A300E288330F500A03098
:1000200008316900107F2000830F4000000F20D101159
:100030000901003189014000010154F0B1528000000
:100040001011000090014242810150009018F513CA
:10005000100101F51F802875080F3982073B283E28AC
:10006000008023B2847286F2880283B284128802863
:100070003B284C285128F50A70081228F50A710807
:1000800001228F30B4428F50A000884A12281015D8
:10009000090014F50AA130102810159014F50AA1301B
:1000A0000100228901400001010150830F40010150314E7
:1000B000090101C0310F10D10119014F40B56287108C8
:1000C0008000840AF30B65286A2890101015000040
:1000D000010115128901410150000101802890145 0
:1000E00000000000010150830F4001015014901C0310C4
:1000F000F10D10119014F40B7428101500001011SC
:100100009010158820908312F51F02340134CA
:100110008008207023341E343A34563472348E3466
:100120000A344C634E234F034820705341E34F43419
:1001300003A342534563441345D342C3448346434F4
:10014000333482070340034003400340034593 42E
:1001500005934593459345365346534653482070034 70
:100160000034063409340 4C340E3412341534193483
:100170001C3482071C3404340C3408341834103412
:100180000C348316003085007030860083121 A10184
:10019000AA01A701BC01BB01BA01BD01B801B901A7
:1001A000B501B601B701A901C101C001BF01BE017E
:1001B000C301C201B001B101CD01CC01CE01CF011B
:1001C000C601051185110512851406148614061 53D
:1001D008615861337142910312722 30AE0059278F
:1001E00031270130300203194429223 0AE0066214 4
:1001F0000013 0AE00A0210230AE00B721000044293 A
:10020000000000730AF0053 27D8230730BC00BD00E3
:100210002F08C100AA01A901B7010C30AE005927 6F
:1002200003127B524AA0120B03EAE000A302E02 62
:100230003190800492 9A9013A2B7010330AE000 84
:100240004523B7010430AE0055233A27B7010530 E6
:100250000AE0064233A27B7010630AE007323B7 011E
:100260000000730AE008223B7010830AE009423B7 01F7
:100270000930AE00AA23080004608908 9420C5004 608AD
:10028000A120D4009726EC280E30AE00592753 2722
:100290003C292E08033C031945232E08043C031 96E
:1002A00055232E08053C031964232E08063C0319 28
:1002B00073232E08073C031945232E08083C03194D8
:1002C0009423 42E08093C0319AA231E2959275327D2
:1002D000530B20081213B244D2410243E08AF00 9C
:1002E0005924342431273914403 0AC003914E525 21
:1002F00039101E30B20099213514371422 30AE 0067
:10030000800C6233B24ED231C272F08BE0092428
:100310000800C6233B2423272F08C10023272F08CA
:10032000C00023272F08BF0023272F08BE0092461
:100330008003B2410243E08AF005924342408005 0
:100340000592753270B30B200C62338143B24 ED2322
:100350009243B2423208053EB200102434243127FE
:100360003810022635143714013 0AE000800592722
:100370005327B24043AF00022208221830B20079
:1003800001C220D221522003C0319722AFC2105308 3
:1003900000AF00022208221830B200D0012222343 0ED
:1003A00000B20022222222222222D30B20142 7D00 7AE
:1003B000000D221522003C0319AB2AFC210630AF00 A8
:1003C000000 222082218 30B200D00122224930B20 0A5
:1003D0000022222222222222D30B200142 7D00 7EC
:1003E0000D221522003C0319F12A29102A14351078
:1003F00037140230AE0008000230AE0059275327F0
:100400003B2408003130AD0059273A273A2708002 D
:100410002330AE00592753270800500 8AF003B247 3
```

APPENDIX-continued

```
:100420003130AD005927532708000130AA003A2780
:10043000291460242A080800D00122222222222224
:1004400022208001427D007512408003B24ED2362
:100450001C272F08BE00092414272A14013C031965
:10046000382A3208B4001530AE00592753273E2AE7
:100470003208B4001630AE005927532760242A08EA
:10048000013C03193E2A3408B2002E08163C031919
:100490004F2A0030B30028275927532708001307E
:1004A000B30028275927532708001E30B200003018
:1004B000D40008002130AE00592731270800AE00D3
:1004C0005927312708002A1429142622AA01A90134
:1004D0000800B2001427013C08003330B200653038
:1004E000D40008005A2211305F221E30B2000030C2
:1004F000D4006322183069220319002213A275A22B6
:1005000012305F2217305F2225530B2000030D40055
:100510006322130F305F2225430B2000030D40055
:100510006322130F306922031900213A275A22123020
:100520005F2218305F222C30B2005930D400632291
:1005300026306922031900213A275A221F30AE00C3
:10054000592731276D2263222D306922031900219A
:100550003A27A901C6295A2211305F221E30B20063
:10056000030D4006322183069220319002213A2791
:100570005A2213305F2217305F223A30B200003027
:10058000D40063223430692203190213A275A2209
:1005900013305F2218305F224130B2005930D4004E
:1005A00063223B306922031900213A275A22133073
:1005B0005F2219305F224830B2005930D4006322E4
:1005C000423069220319002213A275A221F305F2244
:1005D0006D2263222D306922031900213A27A901D7
:1005E000DD295A2211305F221E30B2000030D400C3
:1005F0006322183069220319002213A275A22143045
:100600005F2217305F224F30B2000030D4006322E7
:10061000493069220319002213A275A2214305F22F7
:1006200018305F225630B2005930D4006322503067
:100630006922031900213A275A2214305F22193007
:10064000005F225D30B2005930D400632257306922F6
:10065000031900213A275A2214305F221A305F22F0
:100660006430B2006530D4006322692203190021BE
:100670003A275A221F305F226D2263222D306922D1
:10068000031900213A27A901F929592731273710E1
:10069000040240E305407D06CF23F72349241E24F0
:1006A000351437140330AE00080059273127402491
:1006B00011305407B200D823032445241E243514D6
:1006C00037140430AE000800592731274024123077
:1006D00005407B200D823032445242C24351437149E
:1006E0000530AE000800592731274024124130340745
:1006F000B200D823032445242F24351437140630A3
:10070000AE000800592731274024143035407B200A6
:10071000D823032445242C2445242442F082C243514C5
:1007200037140730AE000800592731270B30AE00D0
:100730003F30AD0016305407B2003127D8230630C1
:10074000BC00BD00032445242C2435143714083084
:10075000AE000800592731273608013C0319B52B94
:100760001530AE0059275327337B92B1630AE00592744
:10077000053270130B700312760243708013C0319A3
:10078000BC2B351437140930AE000800930BC000A
:10079000005300BB000930BA003C30BD0080000930C
:1007A000BC000230BB000030BA001E30BD000800A3
:1007B00000030BB00BA000930BC00BD000800232790
:1007C0002F08C10023272F08C00023272F08BF00B0
:1007D00023272F08BE00092408001C272F08C1006A
:1007E0001C272F08C0001C272F08BF0008001C274B
:1007F0002F08C1001C272F08C00023272F08C30083
:1008000003F30AD0008001C272F08C1003F30AD006D
:1008100080023272F08C30023272F08C2000800041
:10082000037080003C0319B5244108AF00592440089B
:100830008AF00592A43F08AF0059248AF00CA00080034
:100840000319B5244108AF0059244008AF005924CA
:10085000004308AF00592408003708003C0319B524A9
:100860004108AF00592408004308AF00592442084A
:10087000AF00592408000E30AE003F30AD00080034
:10088000D30AE003F30AD0008003208013EB2002E
:1008900008003208033EB20008003208063EB200EB
:1008A00008003208073EB200080030D3EB200D0
:1008B00008002F08B30028275327AD03B203080010
:1008C0000061486140615861586110530A200FF3021
:1008D00A4008F30A300061E782C861E812C061FD4
:1008E000922CA30B6B2CA40B692CA20B672C080079
:1008F00031272908013C03197F2C371008002A10E2
:10090000080031272908013C0319872C08002B080F
```

APPENDIX-continued

```
:10091000B2000130B30028271630AE005927532704
:100920002A14080031272908013C0319A22C360893
:100930000003C0319AD2C0030B6001C30AE00592726
:10094000000532708002B08B2000030B30028271530C9
:10095000AE00592753272A1408000130B6001D3075
:10096000AE005927532731270800061486140615B0
:100970000086158611061E0800861EC12C061FCD2C6A
:10098000BA2C31270304302031992C5C3030030E1
:100990000041020319092DC103DD2C3127C30A3D088B
:1009A000043020319992541083C020319F22CC10A9C
:1009B000013039020319E52DDD2C4108AF0059271C
:1009C0005327003035020319B52EBA2C4008AF006A
:1009D000AD0359275327AD0A5327003035020319B9
:1009E000B52EBA2C0030AF00C10001303902031916
:1009F000FF2C5927532700303B020319BA2C40081B
:100A0003B020319182DC00A013039020319E52DE4
:100A1000E62C3C08C100AF005927532700303B02A9
:100A2000000319BA2C4008003C03194020C003E62CE2
:100A30000030AF00C000013039020319272DAD038B
:100A40000059275327AD0A00303020319BA2C42083D
:100A50000000C3C03199F2D013038020319C12D3F08AA
:100A60003A0203195F2DC20ABF0A01303902031985
:100A70005E2D3F08EE25003035020319B52EBA2CBE
:100A8000B08AF00C000AD0359275327AD0A003023
:100A90003A020319BA2C013038020319DA2D3F0843
:100AA00003C0319842DC203BF03EE254208003C1D
:100AB0000319CC2D003035020319B52EBA2CC20A09
:100AC0000030AF00BF0001303902031972DAD03B2
:100AD000AD0359275327AD0AAD0A01303802031977
:100AE000BA2CBE0A013039020319E52DF725420858
:100AF0000000C3C03199F2D013039020319E52D0030FC
:100B000035020319B52EBA2CC2033A08AF00BF0054
:100B1000AD03AD0359275327AD0AAD0A01303802A2
:100B20000319BA2CBE03F7254208003C0319CC2D4B
:100B3000BA2C003030008003D08C3000800013093
:100B40002C0001130BF00AF00AD03AD030130390278
:100B50000319AC2D59275327AD030030BE00AF0059
:100B60000013039020319B62D592753273F30AD0004
:100B70000003035020319B52E013039020319E52D75
:100B8000BA2C09303F02031D2F2D0630C200BF00D2
:100B9000E825AD0AAD0ABA2C0C30C2000230BF0005
:100BA000E825AD0030130BE00AF00592753273F3081
:100BB000AD00BA2C06303F02031D4F2D0930C20094
:100BC000BF00E825AD0ABA2CAC0B0E2C08004C
:100BD000AF00AD03AD035927532708003F08AF000E
:100BE000AD03AD0359275327AD0AAD0A08003E08EF
:100BF000AF00AD03AD03AD0359275327AD0AAD0ACE
:100C0000AD0A080417D0B30B2003B2423272F080D
:100C1000010023272F08000023272F08BF00092465
:100C20003F08A7000630A70227080030031924E1E
:100C300002708013C0319262E2708023C0319292EF8
:100C40002708033C03192C2E43082E2E43083C3E54
:100C50002E2E4308783E2E2E43083B4E3EB00A8004B
:100C6000A701A70A0330AB020318312E5630A7079D
:100C70001E30B20089218C262530B2009921073020
:100C8000A7078C262C30B20099210730A7078C26A5
:100C90003330B20099212808AB00A701A70A04301D
:100CA000AB0203184E2E3E30A7071E30B20089213A
:100CB00008C263A30B20099210530A7078C264130A6
:100CC000B20099210530A7078C264830B20099213F
:100CD000D200280BAB00A701A70A0530AB0203186B2E4A
:100CE0002F30A7071E30B20089218C264F30B2006A
:100CF00099210430A7078C265630B2009921043080
:100D0000A7078C265D30B20099210430A7078C26F6
:100D10000064630B20099210800270BAC003914E52599
:100D200003910080035808003C03199726080023C06
:100D3000AE0059275327E30AE00532735104608012
:100D40003C03196C01468C6A4508B20046080E
:100D5000A120D400B001C6233B24ED231C272F087B
:100D6000BE0009243B244D24CD2C3608013C03193E
:100D7000C42ED60BC32E861553270611022706153F
:100D80005327861153270227CB260130300203193F
:100D9000800B42E08001830D100E026E52601300C
:100DA0003002031908000730D107E026E52601309C
:100DB0003002031908005108E3C03190800D32EC5
:100DC000510AD200520AD30008005208B200142778
:100DD00004202031D08005308B200142743020231DFA
:100DE00008005108B20014270C3C0319FD2E802F83
:100DF0002230AE0059273A270800C60AA4608A1202B
```

APPENDIX-continued

```
:100E0000D40008003C30A1006230A2003030A400C1
:100E10004530A300A30B0A2F0000A40B082FA20B40
:100E2000062FA10B042F08003208F0000D20F51F3B
:100E3000162F7108000008001427AF00592731272A
:100E4000AD03B20308001427AF00AD03B2030800DE
:100E50003208F0003308F1000520F51F202F0000A8
:100E60000800FF30A400FF30A300A30B352FA40B14
:100E7000332F08000430A200FF30A400FF30A3008D
:100E8000A30B402FA40B3E2FA20B3C2F08003127B1
:100E9000312731273127312708002A30A50093
:100EA000A50B502F08005030A6004E27A60B552F3B
:100EB00008002E08A00063272F08A00063272D0834
:100EC000A000632708008B128B1381016400831636
:100ED000D830810083120830A100851081010B11E8
:100EE0000B1D702F0B11A00D8510031885140B1D01
:100EF000772F0B11A10B732F85140B1D7D2F08006D
:100F00008316023085008312C0305407B200142778
:100F1000B000FF30CB0011305407B2001427A700F7
:100F20008920CA00CB022708AE20CC00B20A1427C1
:100F30008920C800A100B20A14278920C900B20A7A
:100F40001427CF00CE00B20AB20A1427B920D50068
:100F5000B1013114CD01003031020319B12F550810
:100F600085004A08A200CC27003085004B08A2006B
:100F7000CC27A10BAB2FD82F3008003C0319C12F71
:100F8000AB2FB1010130B00046C8043ED6008316F5
:100F9000003085008312F82E00000230A4000330D8
:100FA000A300A30BD12FA40BCF2FA20BCD2F080092
:100FB000013031020319E02F4808A1003114BC2F81
:100FC0004908A100B0033110A10300304D020319FC
:100FD000F22F4C08CA070B02CE0BB02F4F08CE0015
:100FE0004D10BC2F4C08CA02CB07CE0BBC2F4F08AC
:060FF000CE004D14BC2FE1
:00000001FF
```
Pic16ce625.hex EEPROM
The object code for the Pic16ce625 which is to be loaded into the chip or emulator EEPROM memory bank with the program's default values.

```
:020000008D2849
:080008008D288430F5008316F9
:100010004B2880301228F30087301228F3008A30F2
:1000200012288330F500A03083169010F2000830BB
:10003000F4000000F20D101190100318901400004D
:100040001015F40B1928000010110000901428836
:1000500010150000901BF5131011F51F842875086D
:100060000F3982073F28422884283F284B287328CD
:1000700084283F28452884283F2850285528F50AF9
:1000800070081628F50A71081628F30B4828F50A97
:100090000008840A162810159014F50AA1301428B7
:1000A00010159014F50AA1301428901400001015B2
:1000B000830F40010150314901C0310F10D1011FA
:1000C0009014F40B5A2871088000840AF30B6928F5
:1000D0006E289010101500001011552890141015E
:1000E0000000101184289014000010150830F4004E
:1000F00010150314901C0310F10D10119014F40B43
:10010000782810150000101190101015C209014F4
:100110008312F51F02340134080000F30F600AD
:1001200006308A007608F0000026F1000920F51F4D
:100130009228F60A710876087C3C03199E289228BA
:100C000082070A341E340134003403340034063480
:100C100007341E34073403340034023400340234
:100C200003402340340934093409340934094F5
:100C300093400340340034003400340340B
:100C400000340340340034003400340034004
:100C500000340340340034003400340034044
:100C600000340340340034003400340034E4
:100C700000340340340034003400340034D4
:100C800000340340340013400340034003C3
:100C900000340340340034003400340034B4
:100CA000003403403400340034009349B
:100CB0000073403403400340034003409347C
:100CC00000340340340034093409340403472
:100CD000003403403400340034034003474
:100CE000003403403400340034034003464
:0E0CF000034003403400340034003408A
:00000001FF
```

What is claimed is:

1. An apparatus for facilitating the investigation of the subject matter of dreams a user's dreams, the apparatus comprising:
   a micro controller;
   at least one input device operatively connected to the micro controller;
   an alert enunciator operatively connected to the microprocessor;
   said micro controller being adapted to receive a start time corresponding to a time when the user goes to sleep, and an end time corresponding to a time when the user expects to rise,
   said micro controller further adapted to calculate an alert setting temporally associated with the occurrence of a REM event which the user is expected to experience in the time period between the start time and end time; and
   said micro controller adapted to activate said enunciator at a time corresponding to said alert setting.

2. The apparatus of claim 1 wherein said enunciator comprises an aural alert adapted to wake the user during REM sleep.

3. The apparatus of claim 1 wherein said enunciator comprises a visual alert adapted to wake the user during REM sleep.

4. The apparatus of claim 3 wherein said visual alert comprises one or more flashing lights directed toward the user.

5. The apparatus of claim 4 wherein said flashing lights comprise a plurality of differently colored LEDs.

6. The apparatus of claim 3 wherein said visual alert comprises flashing said LEDs for a fixed period of time, said LEDs flashing at a pulse frequency, each pulse having a pulse length and a pulse intensity for a fixed period of time.

7. The apparatus of claim 6 wherein at least one of said frequency, pulse length and pulse intensity may be selected by the user.

8. The apparatus of claim 1 wherein said micro controller is configured to calculate a plurality of alert settings, each alert setting being temporally associated with a different REM event calculated to occur between the start time and end time.

9. The apparatus of claim 1 further comprising a voice activated dictation system whereby the user may record statements upon being awakened by said enunciator.

10. An apparatus for facilitating the remembrance of a user's dreams comprising:
    means for receiving input data related to the start time and end time of a sleep period;
    means for calculating times when REM events are likely to occur;
    means for selectably waking the user during the periods when REM events have been calculated as being likely to occur; and
    means for recording the subject matter of the user's dreams when the user is awakened during the course of REM events.

11. The apparatus of claim 10 wherein said means for recording the subject matter of the user's dreams comprises a microphone operatively connected to a record/playback chip whereby voice messages may be selectively recorded and played back of over a speaker operatively connected to the record/playback chip.

12. The apparatus of claim 10 wherein the means for receiving input data comprises a plurality of input switches operatively connected to a micro controller.

13. The apparatus of claim 10 further comprising a micro controller, said micro controller configured to calculate the times at which REM events are likely to occur and drive a plurality of flashing LEDs at the times at which REM events have been calculated as being likely to occur.

14. The apparatus of claim 13 wherein the pulse rate at which said LEDs flash is selectable.

15. The apparatus of claim 13 wherein the length of each pulse of the flashing LEDs is selectable.

16. The apparatus of claim 13 wherein the length of time between the pulsed of said flashing LEDs is selectable.

17. The apparatus of claim 13 further comprising a plurality of red, green and blue LEDs, such that an overall color of the flashing LEDs is selectable.

18. The apparatus of claim 13 wherein the number of REM events likely to occur is selectable.

19. The apparatus of claim 10 further comprising a first micro controller having a plurality of programmable operating parameters, and an LCD screen adapted to display messages prompting the user to enter values for said programmable operating parameters.

20. An apparatus for facilitating the remembrance of a user's dreams comprising:

means for receiving input data related to the start time and end time of a sleep period;

means remote from the user for determining when REM events are likely to be occurring;

means for selectably waking the user during the periods when REM events have been calculated as being likely to occur; and means for recording the subject matter of the user's dreams when the user is awakened during the course of REM events.

* * * * *